US012643851B2

(12) United States Patent
Datla et al.

(10) Patent No.: US 12,643,851 B2
(45) Date of Patent: Jun. 2, 2026

(54) VITAMIN D3 AND ITS ANALOGUE CALCIFEDIOL FROM ERGOSTEROL

(71) Applicant: FERMENTA BIOTECH LIMITED, Thane (IN)

(72) Inventors: Anupama Datla, Thane (IN); Prashant Nagre, Thane (IN); Jagdish Tamore, Thane (IN); Manojkumar Sadanand Prabhu, Thane (IN); Sachin Vasant Kadam, Thane (IN)

(73) Assignee: FERMENTA BIOTECH LIMITED, Thane West (IN)

( * ) Notice: Subject to any disclaimer, the term of this patent is extended or adjusted under 35 U.S.C. 154(b) by 1119 days.

(21) Appl. No.: 17/621,075

(22) PCT Filed: Jul. 2, 2020

(86) PCT No.: PCT/IN2020/050577

§ 371 (c)(1),
(2) Date: Dec. 20, 2021

(87) PCT Pub. No.: WO2021/005619

PCT Pub. Date: Jan. 14, 2021

(65) Prior Publication Data

US 2022/0267266 A1 Aug. 25, 2022

(30) Foreign Application Priority Data

Jul. 9, 2019 (IN) ............................. 201921027407

(51) Int. Cl.
*C07C 401/00* (2006.01)
*C07F 7/18* (2006.01)
*C07J 9/00* (2006.01)

(52) U.S. Cl.
CPC .......... *C07C 401/00* (2013.01); *C07F 7/1804* (2013.01); *C07J 9/00* (2013.01); *C07C 2602/24* (2017.05)

(58) Field of Classification Search
CPC .......... C07C 401/00; C07F 7/1804; C07J 9/00
See application file for complete search history.

(56) References Cited

U.S. PATENT DOCUMENTS 5,252,191 A * 10/1993 Pauli .................... C07D 409/04
204/157.67

FOREIGN PATENT DOCUMENTS

| | | | |
|---|---|---|---|
| EP | 1103300 B1 | | 1/2007 |
| WO | 92/12165 A1 | | 7/1992 |
| WO | WO2016103722 A1 | * | 6/2016 |

OTHER PUBLICATIONS

Fuse et al, Continuous-flow synthesis of activated vitamin D3 and its analogues, 2012, Organic & Biomolecular Chemistry, vol. 10, p. 5205-5211. (Year: 2012).*

Zala et al, Laboratory Techniques of Purification & Isolation, 2012, Int. J. Drug Dev & Res, vol. 4, No. 2, p. 41-55 (Year: 2012).*

Fischer, Synthesis of C25- and C26-Steroid Carboxylic Acids from C22-steroids Using Nickelacycles as Propionic and Butyric Acid Equivalents, 1993, Synthesis, vol. 12, p. 1267-1270. (Year: 1993).*

Scherlitz-Hofinann et.al., "Synthesis of 25-Hydroxypro vitamin D3 form Ergosterol: A Mild Method for the Cleavage of Hetero Diels Alder Adducts Leading to Steroidal 5,7 Dienes," Synthesis 1999, No. 8, 1331-1334.

Fischer et al., "Synthesis of C25- and C26-Steroid Carboxylic Acids from C22-Steroids Using Nickelacycles as Propionic and Butyric Acid Equivalents," Synthesis 1993; 1993(12): 1267-1270.

* cited by examiner

*Primary Examiner* — Adam C Milligan
*Assistant Examiner* — Karen Cheng
(74) *Attorney, Agent, or Firm* — Kramer & Amado, P.C.

(57) ABSTRACT

Disclosed herein is an improved and efficient process for synthesis of vitamin D3 and its analogue Calcifediol from Ergosterol. Particularly, the present invention discloses the synthesis of key intermediate 3β-tert-Butyldimethylsilyloxy-22-hydroxy-23,24-bisnorchola-5,7-diene (5), and novel intermediate β-tert-Butyldimethylsilyloxy-22-iodo-23,24-bisnorchola-5,7-diene (9) by a simple and cost effective process. The industrially viable processes for preparation of said intermediate(s) results in providing provitamins with various side chains and the desired products in high yield.

14 Claims, No Drawings

VITAMIN D3 AND ITS ANALOGUE CALCIFEDIOL FROM ERGOSTEROL

TECHNICAL FIELD OF INVENTION

The present invention relates to an improved and efficient process for synthesis of vitamin D3 and its analogue Calcifediol from Ergosterol. Particularly, the present invention relates to the synthesis of key intermediate 3β-tert-Butyldimethylsilyloxy-22-hydroxy-23,24-bisnorchola-5,7-diene (5), under mild reaction conditions that leads to the formation of stable free 5,7 diene system of said intermediate in quantitative yield. The present invention further provides a novel intermediate β-tert-Butyldimethylsilyloxy-22-iodo-23,24-bisnorchola-5,7-diene (9) prepared from the intermediate (5) by a simple, cost effective process. The industrially viable processes for preparation of said intermediate(s) results in providing provitamins with various side chains and the desired products in high yield.

BACKGROUND AND PRIOR ART

Vitamin D3 (cholecalciferol) is the naturally occurring form of vitamin D produced in the skin after 7-dehydrocholesterol is exposed to solar UV radiation. Vitamin D2 (ergocalciferol) is produced synthetically by UV irradiation of ergosterol. The two forms differ in the structures of their side chains, but they are metabolized identically in the liver and kidney in to 1α,25-(OH) 2-vitamin D3 (activated vitamin D3) which has equivalent broad spectrum of biological activities such as cell differentiation, regulation of calcium metabolism and immune function.

Activated Vitamin D3 and its analogues are clinically used as drugs for various kinds of diseases including renal failure, oesteoporosis, psoriasis and secondary hyperparathyrodism. They are also used for fortification of dairy products. Without a doubt, the most exciting development in vitamin D nutrition in recent years has been the commercialization of 25-OH vitamin D3 in poultry feeds.

Therefore development of a facile method for the synthesis of vitamin D3 and its analogues is highly important.

Ergosterol is a suitable and unique commercially available starting material for the synthesis of such compounds because it exhibits the conjugated 5,7-diene system (provitamin stage) necessary for photochemical isomerization to the previtamin stage, and also a side chain double bond, which can be cleaved by ozonization after protection of the 5,7-diene system by hetero Diels-Alder reaction giving functionalized C22 steroids. After deprotection of the 5,7-diene these C-22 steroids can react with suitable alkyl reagents to provide provitamins with various side chains.

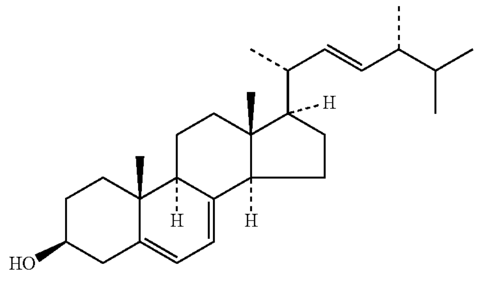

Ergosterol

Article titled "Synthesis of 25-Hydroxyprovitamin D3 form Ergosterol: A Mild Method for the Cleavage of Hetero Diels-Alder Adducts Leading to Steroidal 5,7 Dienes" by Ina Scherlitz-Hofmann et.al. published in Synthesis 1999, No. 8, 1331-1334 discloses seven-step procedure for synthesis of 3β,25-dihydroxy-cholesta-5,7-diene (7) from ergosterol (1). The 3-hydroxy function of ergosterol is protected as tert-butyl dimethylsilyl ether and the 5,7-diene system as hetero Diels-Alder adduct with 1,4-dihydrophthalazine-1,4-dione before ozonization of the side chain double bond. Cleavage of the hetero Diels-Alder adduct is carried out using lithium naphthalenide. Tosylation of the 22-hydroxy function, C—C coupling with a C5 copper reagent and desilylation furnishes the title compound as shown below in Scheme 1.

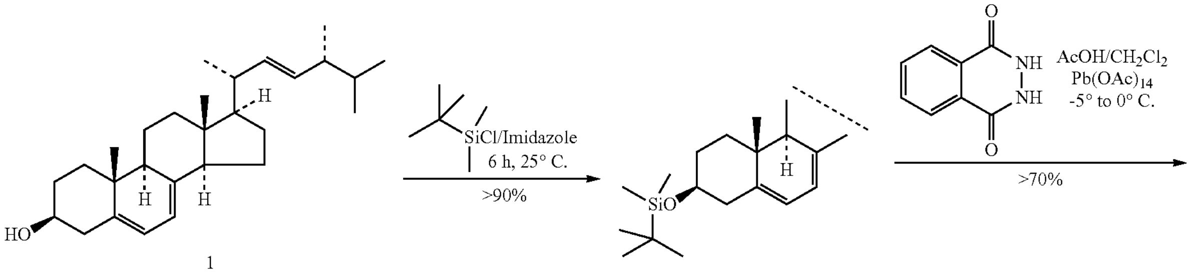

1

2

-continued

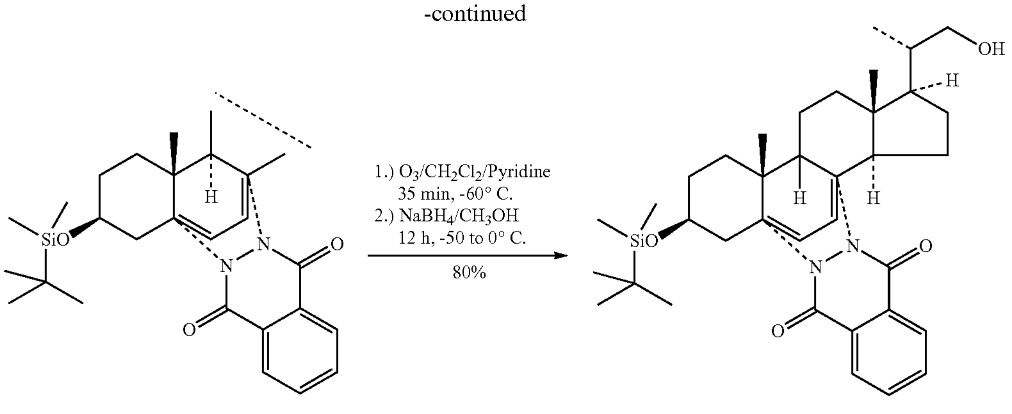

3 4

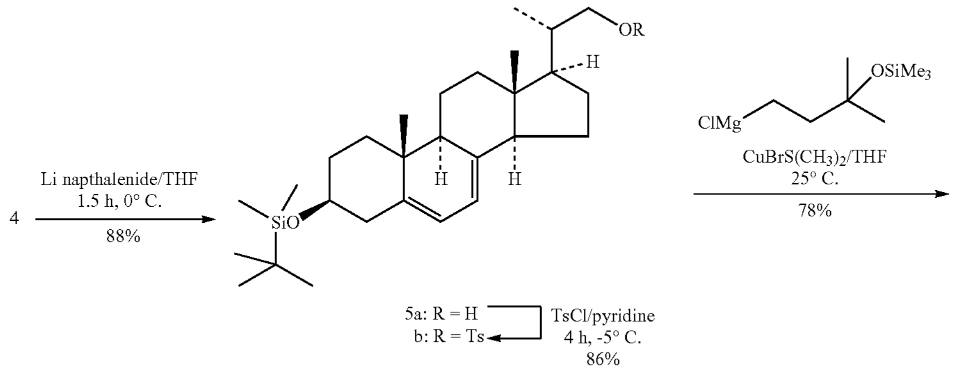

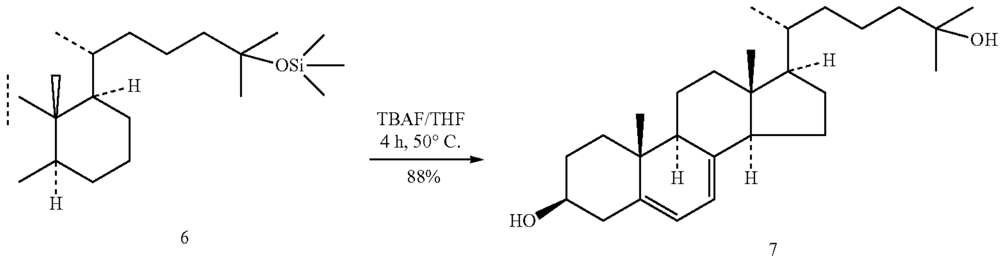

6 7

The article on page 1333, para 1, left column, states that after conversion of the compound (5b) into its corresponding 22-iodide, coupling with nickelalactones yields products suitable for synthesis of provitamins with homologated chains.

The literature titled "Synthesis of C25-and C26-Steroid Carboxylic acids from C22-steroids using Nickelacycles as propionic and butyric acid equivalents" by R. Fischer, published in Synthesis, December 1993 discloses C25 and C26 steroid carboxylic acids and their methyl or ethyl esters from C22 iodides using nickelacycles as propionic and butyric acid equivalents. The C-22 iodides are synthesized from corresponding tosylates by conversion with sodium iodide in DMF. Iodides are converted to carboxylic acids or ester using nickelacyle which again are synthesized from (2,2'-bipyridyl)cycloocta-1,5-diene)-nickel(0) and succinic anhydride. This nickelacycle complex reacts with steroid C-22 iodide in presence of mangenese iodide. Reaction time requires longer duration ~48 h or reaction is to be carried out in ultra sound sonicator. Further obtained acid is to be esterified using diazomethane in diethyl ether.

WO92/12165 titled "Methods for preparation and use of 1α,24-dihydroxy Vitamin D2" discloses a method of preparing 1α, 24-dihydroxy Vitamin D2 comprising (a) acetylating ergosterol to form its 3-acetate; (b) reacting with a triazoline dione and ozonating to form the 22-aldheyde adduct; (c) adding 3-methylbutan-2-one to obtain 22-oxo adduct; (d) adding methyl magnesium bromide to form ergostadiene-3ss,24-diol adduct; (e) reducing to form 24-hydroxy ergosterol; (f) irradiating to form 24-hydroxy vitamin D2; (g) tosylating; (h) solvolyzing to form 24hydroxy-3,5 cyclovitamin D2; (i) allylically oxidizing to form 24 dihydroxy cyclovitamin D2 and hydrolysisng, forming Diels Alder adduct to yield 1α,24 dihydroxy vitamin D2.

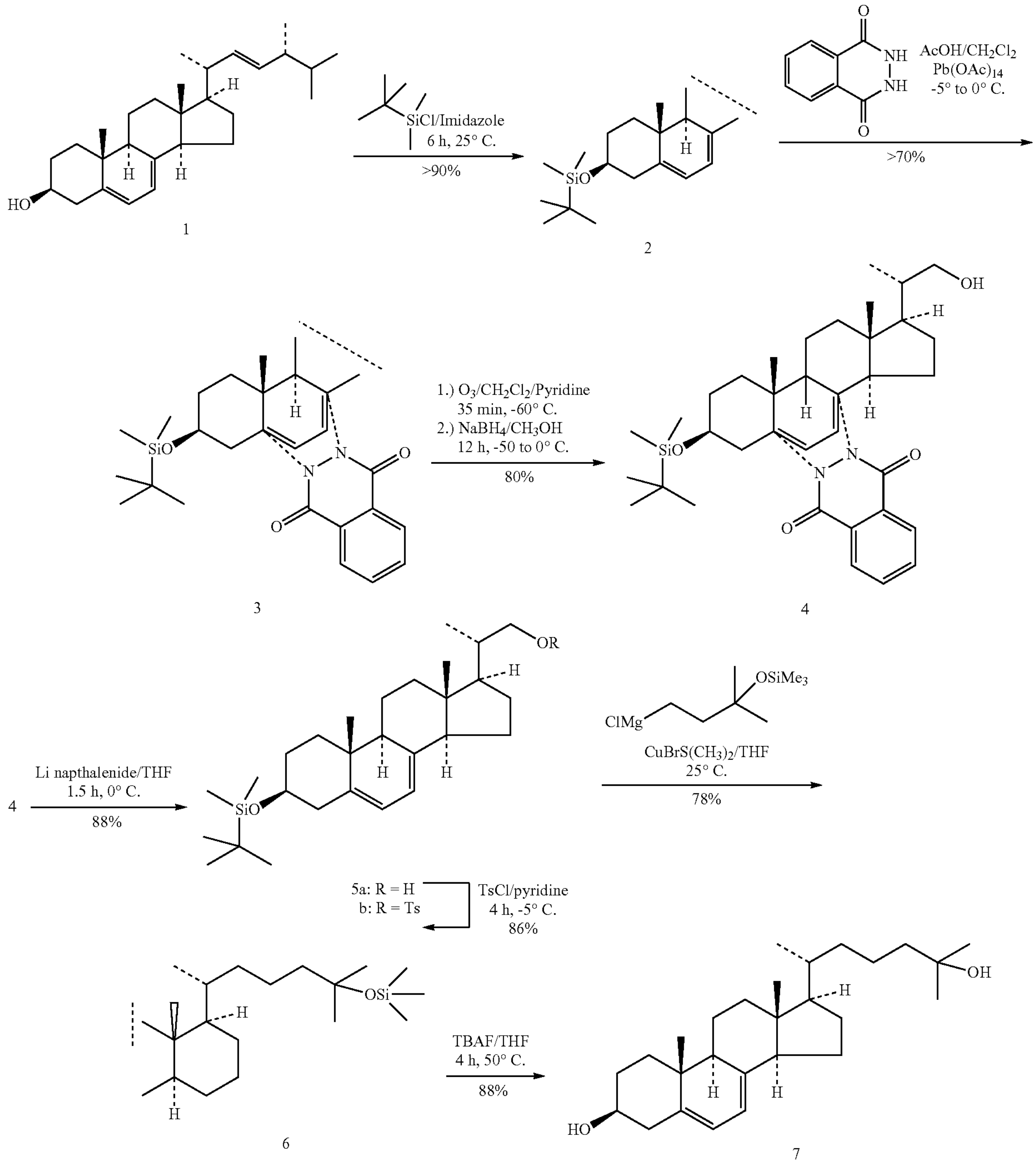

EP1103300B1 discloses a process for preparing a vitamin D derivative by irradiating a solution of provitamin D derivative with ultra-violet rays having specific wavelength selected by the optical filter, through a quartz rod, by means of particular irradiation apparatus thereby converting the provitamin D derivative into a previtamin derivative or further subjecting the previtamin D derivative to a thermal isomerization reaction to prepare vitamin D derivative. EP'300 discloses various derivatives such as (6Z)-(1S,3R,20S)-20-(3-hydroxy-3-methylbutoxy)-9,10-secopregna-5 (10),6,8-triene-1,3-diol (Maxacalcitol, 22-Oxacalcitriol, example 1&2), (6Z)-(1S,3R,20S)-9,10-secocholesta-5(10),6,8-triene-1,3-diol (Alfacalcidiol, example 3), (6Z)-(1S,2R,3R,20S)-2-(3-hydroxypropoxy)-9,10-secocholesta-5 (10),6,8-triene-1,3,25-triol (Eldecalcitol, example 4), pre-vitamin D2, pre-vitamin D3. EP'300 however has not disclosed preparation of calcifediol.

Disadvantages of the Art

In WO92/12165, Diels Alder reaction was carried out using 4-phenyl-1,2,4-triazoline-3,5-dione which is not commercially easily available and the high cost of the reagent renders the process uneconomical.

In the article titled "Synthesis of 25-Hydroxyprovitamin D3 form Ergosterol: A Mild Method for the Cleavage of Hetero Diels-Alder Adducts Leading to Steroidal 5,7 Dienes" two-step process is reported to obtain de-protected 22-OH product 5a or 5b. The first step comprises reduction of aldehyde to 22-OH using $NaBH_4$ at low temperature −50° C.

The temperature plays a key role and should be maintained at about −50° C. during addition of methanol. The reaction is not clean so purification by column chromatography is necessary before de-protection. In the second step de-protection of Hetero Diels-Alder adduct is carried out using Lithium Naphthalenide which is costly reagent and not commercially feasible. Further, though the reaction proceeds well with freshly prepared Lithium Naphthalenide, the preparation of the said reagent is time consuming and has to be stored in argon filled glove box at room temperature which makes the process uneconomical. Moreover, the de-protected 22-OH obtained by the process disclosed in the said article requires further purification by column chromatography adding to the cost of the process (ref: examples on page 1333)

The above article does not disclose the preparation of vitamin D3 from ergosterol.

In the literature titled "Synthesis of C25-and C26-Steroid Carboxylic acids from C22-steroids using Nickelacycles as propionic and butyric acid equivalents" the process requires fresh preparation of Nickelacycle since it is commercially not readily available. The article discloses the direct preparation from nickel acetylacetonate, 2,2'-bipyridyl, triethyl aluminium and succinic anhydride, however, the preparation requires more precaution. The reagent triethyl aluminium is a volatile liquid, highly pyrophoric, ignites immediately on exposure to air and hence handling of this reagent is difficult and not advisable on large scale. Moreover, the reagent is not freely available. Further, reaction of nickelacycle with C22-iodide in presence of manganese iodide takes longer duration and by-product i.e. methylene compound due to beta elimination is also obtained. The esterification reaction using diazomethane in ether is very hazardous reaction, needs special precaution and is industrially not viable.

The processes in the art are cumbersome, uneconomical, the reagents used are not readily available or are highly hazardous which requires extra precaution in handling them, are industrially not viable.

In view of the above, the present inventors felt that there is a scope to provide an improved and efficient process for synthesis of vitamin D3 and its analogue calcifediol from ergosterol by ameliorating the shortfalls of the prior art process. The present disclosure provides a process for synthesis of vitamin D3 and its analogue calcifediol from ergosterol using safe, and easily available chemical reagents, minimizing the side-reactions and side-products by employing optimum reaction conditions.

Particularly, the objective of the present invention is to provide an improvement in the synthesis of certain key intermediate(s) using less expensive, easily available reagents and employing optimal reaction conditions which advantageously contribute to the overall economy of the synthesis of vitamin D3 and its analogue calcifediol from ergosterol.

SUMMARY OF THE INVENTION

According to the above objectives, the present invention provides an improved, cost effective process for synthesis of one of the key intermediate 3β-tert-Butyldimethylsilyloxy-22-hydroxy-23,24-bisnorchola-5,7-diene (5) of C-22 steroids under mild reaction conditions in quantitative yields which can subsequently be used to react with suitable reagents to produce provitamins with desired side chains.

In an aspect, the present invention provides an improved, cost effective process for the conversion of ergosterol to vitamin D3 and its analogue, calcifediol of general formula (I)

(I)

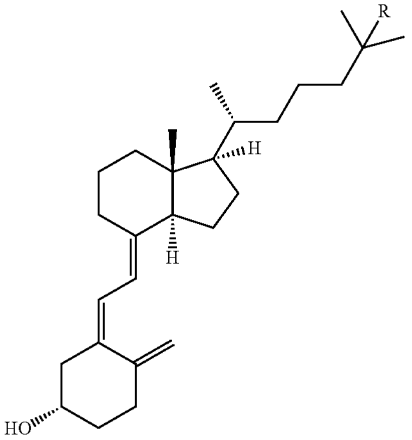

R = H: vitamin D3
R = OH: 25-OH-vitamin D3 (Calcifediol)

via the provitamin precursor of general formula (II)

(II)

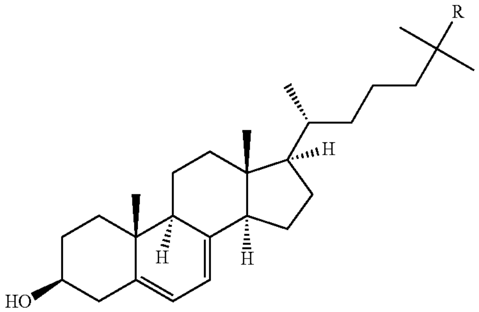

7 or 8
R = H, Provitamin D3 (7)
R-OH, 25-OH provitamin in D3 (8)

which comprises;

converting Ergosterol to Diels Alder adduct, 3β-tert-Butyldimethylsilyloxy-5α,8α-(1,4-dioxo-1,2,3,4-tetrahydro-phthalazine-2,3-diyl)-23,24-bisnorchol-6-en-22-al by (4) known process;

i. Deprotecting Diels Alder adduct, 3β-tert-Butyldimethylsilyloxy-5α,8α-(1,4-dioxo-1,2,3,4-tetrahydro-phthalazine-2,3-diyl)-23,24-bisnorchol-6-en-22-al (4) and reducing the aldehyde to 22-OH in one step with $LiAlH_4$ to obtain the intermediate 3β-tert-Butyldimethylsilyloxy-22-hydroxy-23,24-bisnorchola-5,7-diene (5);

ii. Tosylating the intermediate (5) of step (ii) to obtain the intermediate 3β-tert-Butyldimethylsilyloxy-22-tosyloxy-23,24-bisnorchola-5,7-diene (6);

iii. Converting the intermediate (6) to provitamin precursor of general formula (II); and iv. Irradiating the pro-vitamin precursor of formula (II) in presence of photosensitizer to obtain compounds of formula (I) followed by crystallization.

In another aspect, the present invention provides an improved and cost effective process for synthesis of intermediate 3β-tert-Butyldimethylsilyloxy-22-hydroxy-23,24-bisnorchola-5,7-diene (5) from ergosterol comprising Deprotecting 3β-tert-Butyldimethylsilyloxy-5α,8α-(1,4-dioxo-1,2,3,4-tetrahydro-phthalazine-2,3-diyl)-23,24-bisnorchol-6-en-22-al (4) and reducing the aldehyde to 22-OH in one step with $LiAlH_4$ in THF at 45° C. for 3 hours to obtain the intermediate 3β-tert-Butyldimethylsilyloxy-22-hydroxy-23,24-bisnorchola-5,7-diene (5).

In another aspect, the present invention provides an improved, cost effective process for the conversion of ergosterol to vitamin D3 and its analogue, calcifediol of Formula (I)

(I)

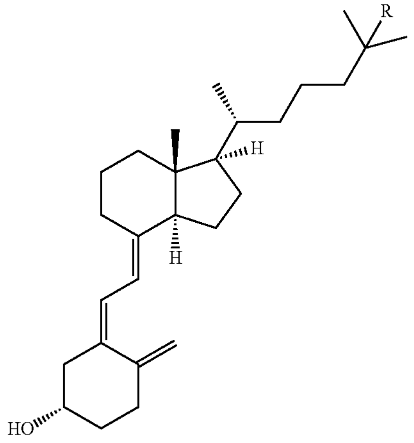

R = H: vitamin D3
R-OH: 25-OH-vitamin D3 (Calcifediol)

via the provitamin precursor, 7-DHC of formula (IIA), (IIA)

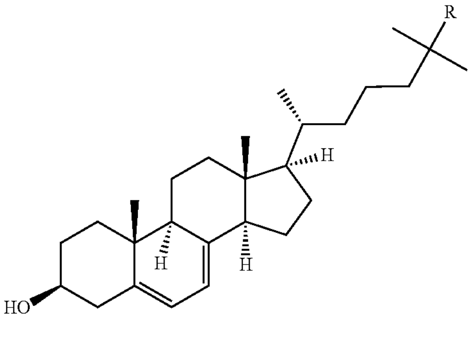

(wherein R=H)
comprising;

Converting Ergosterol to Diels Alder Adduct, 3β-tert-Butyldimethylsilyloxy-5α,8α-(1,4-dioxo-1,2,3,4-tetrahydro-phthalazine-2,3-diyl)-23,24-bisnorchol-6-en-22-al (4) by known process;

i. Deprotecting Diels Alder adduct, 3β-tert-Butyldimethylsilyloxy-5α,8α-(1,4-dioxo-1,2,3,4-tetrahydro-phthalazine-2,3-diyl)-23,24-bisnorchol-6-en-22-al (4) and reducing the aldehyde to 22-OH in one step with $LiAlH_4$ to obtain the intermediate 3β-tert-Butyldimethylsilyloxy-22-hydroxy-23,24-bisnorchola-5,7-diene (5);

ii. Tosylating the intermediate (5) of step (i) to obtain the intermediate 3β-tert-Butyldimethylsilyloxy-22-tosyloxy-23,24-bisnorchola-5,7-diene (6);

iii. Reacting the intermediate (6) with Grignard reagent of 1-Bromo-3-methylbutane in presence of $CuBr{\cdot}Me_2S$ followed by desilylation with TBAF in THF to obtain 7-DHC of Formula (IIA); and iv. Irradiating 7-DHC (IIA) in presence of photosensitizer to compounds of Formula (I) followed by crystallization.

In yet another aspect, the present invention provides an improved, cost effective process for the conversion of ergosterol to vitamin D3 and its analogue, calcifediol of Formula (I)

(I)

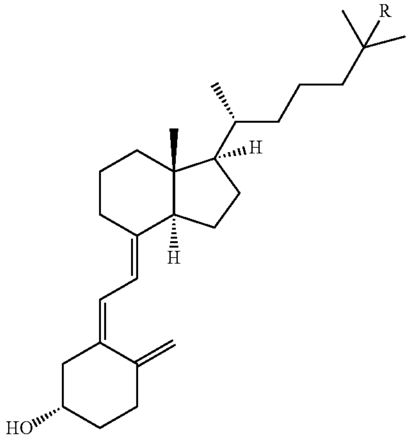

R = H: vitamin D3
R-OH: 25-OH-vitamin D3 (Calcifediol)

via the provitamin precursor of general formula (IIB)

(IIB)

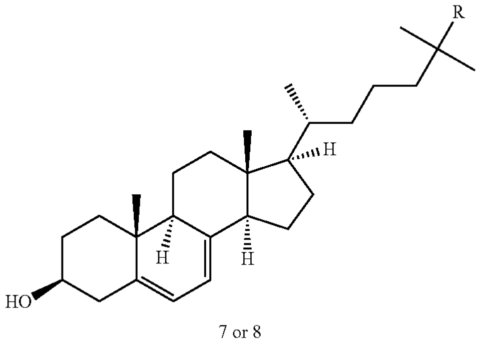

7 or 8
R = H, Provitamin D3 (7)
R-OH, 25-OH provitamin in D3 (8)

(wherein R=OH) comprising;

i. Converting Ergosterol to Diels Alder Adduct, 3β-tert-Butyldimethylsilyloxy-5α,8α-(1,4-dioxo-1,2,3,4-tetrahydro-phthalazine-2,3-diyl)-23,24-bisnorchol-6-en-22-al (4) by known process;

ii. Deprotecting Diels Alder adduct of step (i), 3β-tert-Butyldimethylsilyloxy-5α,8α-(1,4-dioxo-1,2,3,4-tetrahydro-phthalazine-2,3-diyl)-23,24-bisnorchol-6-en-22-al (4) and reducing the 22-aldehyde to 22-OH in one step with $LiAlH_4$ to obtain the intermediate 3β-tert-Butyldimethylsilyloxy-22-hydroxy-23,24-bisnorchola-5,7-diene (5);

iii. Tosylating the intermediate (5) of step (i) to obtain the intermediate 3β-tert-Butyldimethylsilyloxy-22-tosyloxy-23,24-bisnorchola-5,7-diene (6);

iv. Reacting the intermediate (6) of step (ii) with Grignard reagent of 4-bromo-2-methyl-2-[(trimethylsilyl)oxy] butane and $CuBr{\cdot}SMe_2$ followed by desilylation to obtain 25-OH provitamin D3 of formula (IIB); and v. Irradiating 25-OH provitamin D3 (IIB) in presence of photosensitizer to obtain compounds of formula (I) followed by crystallization.

In another aspect, the present invention provides the novel iodo intermediate, 3β-tert-Butyldimethylsilyloxy-22-iodo-23,24-bisnorchola-5,7-diene (9) for preparation of vitamin D3 and its analogue calcifediol of general formula (I) from ergosterol.

The intermediate, 3β-tert-Butyldimethylsilyloxy-22-iodo-23,24-bisnorchola-5,7-diene (9), is prepared from the intermediate 3β-tert-Butyldimethylsilyloxy-22-hydroxy-23,24-bisnorchola-5,7-diene (5), via the intermediate 3β-tert-Butyldimethylsilyloxy-22-tosyloxy-23,24-bisnorchola-5,7-diene (6) which is further reacted with NaI/acetone or alternately by direct iodination.

Accordingly, the improved, cost effective process for preparation of vitamin D3 and its analogue, calcifediol of Formula (I)

(I)

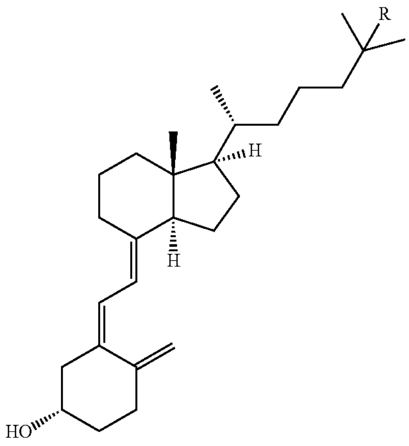

R = H: vitamin D3
R-OH: 25-OH-vitamin D3 (Calcifediol)

from ergosterol, via the precursor 25-OH provitamin D3 (IIB) comprises;

i. Tosylating the intermediate (5) of step (i) to obtain the intermediate 3β-tert-Butyldimethylsilyloxy-22-tosyloxy-23,24-bisnorchola-5,7-diene (6);

ii. Reacting intermediate 3β-tert-Butyldimethylsilyloxy-22-tosyloxy-23,24-bisnorchola-5,7-diene (6) with NaI/acetone at reflux to obtain the intermediate 3β-tert-Butyldimethylsilyloxy-22-iodo-23,24-bisnorchola-5,7-diene (9);

iii. Alkylating the intermediate (9) with Ni(0) complex derived from ethyl acrylate in-situ to yield the intermediate ester, Ethyl-3β-tert-Butyldimethylsilyloxy-chola-5,7-diene-24-carboxylate (10);

iv. Reacting the ester (10) with Grignard reagent to obtain 3β-tert-Butyldimethylsilyloxy-25-hydroxychola-5,7-diene (11) followed by desilylation to yield 25-OH provitamin D3 (IIB); and v. Irradiating 25-OH provitamin D3 (IIB) in presence of photosensitizer to obtain compounds of formula (I) followed by crystallization.

In yet another aspect, the iodo intermediate, 3β-tert-Butyldimethylsilyloxy-22-iodo-23,24-bisnorchola-5,7-diene (9) may be directly obtained by reacting the intermediate 3β-tert-Butyldimethylsilyloxy-22-hydroxy-23,24-bisnorchola-5,7-diene (5) with $PPh_3/I_2$ in imidazole.

Accordingly, the present invention provides an improved, cost effective process for preparation of vitamin D3 and its analogue, calcifediol of formula (I)

(I)

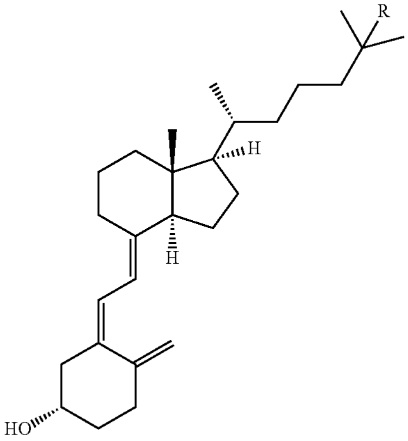

R = H: vitamin D3
R-OH: 25-OH-vitamin D3 (Calcifediol)

from ergosterol, via the precursor 25-OH provitamin D3 (IIB) comprising;

i. Converting Ergosterol to Diels Alder Adduct, 3β-tert-Butyldimethylsilyloxy-5α,8α-(1,4-dioxo-1,2,3,4-tetrahydro-phthalazine-2,3-diyl)-23,24-bisnorchol-6-en-22-al (4) by known process;

ii. Deprotecting Diels Alder adduct, 3β-tert-Butyldimethylsilyloxy-5α,8α-(1,4-dioxo-1,2,3,4-tetrahydro-phthalazine-2,3-diyl)-23,24-bisnorchol-6-en-22-al (4) and reducing the 22-aldehyde to 22-OH in one step with $LiAlH_4$ to obtain the intermediate 3β-tert-Butyldimethylsilyloxy-22-hydroxy-23,24-bisnorchola-5,7-diene (5);

iii. Reacting intermediate (5) with $PPh_3/I_2$ in imidazole to obtain 3β-tert-Butyldimethylsilyloxy-22-iodo-23,24-bisnorchola-5,7-diene (9);

iv. Alkylating the intermediate (9) with Ni(0) complex derived from ethyl acrylate in-situ to yield the intermediate ester, Ethyl-3β-tert-Butyldimethylsilyloxy-chola-5,7-diene-24-carboxylate (10);

v. Reacting the ester (10) with Grignard reagent to obtain 3β-tert-Butyldimethylsilyloxy-25-hydroxychola-5,7-diene (11) followed by desilylation to yield 25-OH provitamin D3 of formula (IIB); and vi. Irradiating 25-OH provitamin D3 (IIB) in presence of photosensitizer to obtain compounds of formula (I) followed by crystallization.

In an aspect, the present invention provides an improved, cost effective process for conversion of ergosterol to vitamin D3 and its analogue calcifediol of formula (I)

(I)

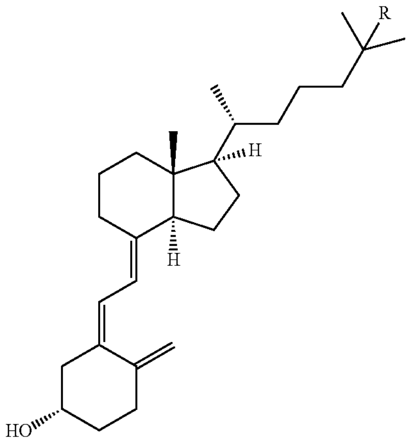

R = H: vitamin D3
R-OH: 25-OH-vitamin D3 (Calcifediol)

via the provitamin precursor of general formula (II)

(II)

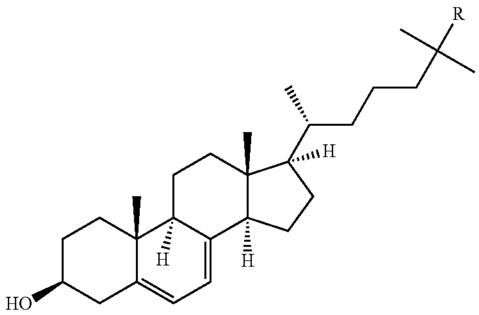

7 or 8
R = H, Provitamin D3 (7)
R-OH, 25-OH provitamin in D3 (8)

comprising, i. Silylating the 3β-hydroxyl group of ergosterol to obtain the intermediate 3β-tert-Butyldimethylsilyloxy-ergosta-5,7,22-triene (2);
ii. Carrying out the hetero Diels-Alder reaction of intermediate (2) with 1,4-dihydrophthalazine-1,4-dione, prepared in-situ, to obtain the Diels Alder adduct, 3β-tert-Butyldimethylsilyloxy-ergosta-5,7,22-triene-5α,8α-(1,4-dioxo-1,2,3,4-tetrhydro phthalazine-2,3-diyl) ergosta-6,22-diene (3);
iii. Ozonolysis of the adduct (3) to obtain 3β-tert-Butyldimethylsilyloxy-5α,8α-(1,4-dioxo-1,2,3,4-tetrahydro-phthalazine-2,3-diyl)-23,24-bisnorchol-6-en-22-al (4);
iv. Deprotecting Diels Alder adduct, and reducing the 22-aldehyde to 22-OH of 3β-tert-Butyldimethylsilyloxy-5α,8α-(1,4-dioxo-1,2,3,4-tetrahydro-phthalazine-2,3-diyl)-23,24-bisnorchol-6-en-22-al (4) n one step with $LiAlH_4$ to obtain the intermediate 3β-tert-Butyldimethylsilyloxy-22-hydroxy-23,24-bisnorchola-5,7-diene (5);
v. Tosylating the intermediate (5) of step (i) to obtain the intermediate 3β-tert-Butyldimethylsilyloxy-22-tosyloxy-23,24-bisnorchola-5,7-diene (6);
vi. Converting the intermediate (6) to provitamin precursor of formula (II); and
vii. Irradiating the provitamin precursor of formula (II) in presence of photosensitizer to obtain n compounds of formula (I) followed by crystallization.

In an aspect, the improved, cost effective process for preparation of vitamin D3 and its analogue calcifediol of formula (I) from the intermediate, 3β-tert-Butyldimethylsilyloxy-22-hydroxy-23,24-bisnorchola-5,7-diene (5); comprising:

i. Tosylating the intermediate (5) of step (i) to obtain the intermediate 3β-tert-Butyldimethylsilyloxy-22-tosyloxy-23,24-bisnorchola-5,7-diene (6);
ii. Reacting the intermediate (6) with Grignard reagent of 1-Bromo-3-methylbutane in presence of $CuBr{\cdot}Me_2S$ followed by desilylation with TBAF to obtain 7-DHC of Formula (IIA);

OR iii. Reacting the intermediate (6) of step (ii) with 4-bromo-2-methyl-2-[(trimethylsilyl)oxy]butane and $CuBr{\cdot}SMe_2$ followed by desilylation to obtain 25-OH provitamin D3 of formula (IIB);
iv. Irradiating the precursors of formula (IIA) and (IIB) in presence of photosensitizer to compounds of Formula (I) followed by crystallization.

In yet another aspect, the improved, cost effective process for preparation of vitamin D3 and its analogue calcifediol of formula (I) from intermediate, 3β-tert-Butyldimethylsilyloxy-22-hydroxy-23,24-bisnorchola-5,7-diene (5), comprises:

i. converting the intermediate (5) to 3β-tert-Butyldimethylsilyloxy-22-iodo-23,24-bisnorchola-5,7-diene (9) by direct iodination with $PPh_3/I_2$ in imidazole;

OR ii. tosylating compound (5) to intermediate 3β-tert-Butyldimethylsilyloxy-22-tosyloxy-23,24-bisnorchola-5,7-diene (6) followed by iodination with NaI/acetone to obtain intermediate 3β-tert-Butyldimethylsilyloxy-22-iodo-23,24-bisnorchola-5,7-diene (9);
iii. Alkylating the intermediate (9) with Ni(0) complex derived from ethyl acrylate in-situ to yield the intermediate ester, Ethyl-3β-tert-Butyldimethylsilyloxy-chola-5,7-diene-24-carboxylate (10);
iv. Reacting the ester (10) with Grignard reagent to obtain 3β-tert-Butyldimethylsilyloxy-25-hydroxychola-5,7-diene (11) followed by desilylation to yield 25-OH provitamin D3 of formula (IIB); and
v. Irradiating 25-OH provitamin D3 (IIB) in presence of photosensitizer to obtain compound of formula (I) followed by crystallization.

In an aspect, the present invention provides the novel intermediate, 3β-tert-Butyldimethylsilyloxy-22-iodo-23,24-bisnorchola-5,7-diene (9) comprising:

9

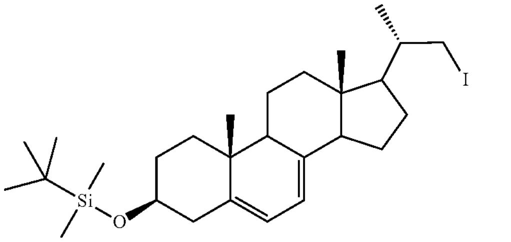

In yet another aspect, the present invention provides the novel intermediate, Ethyl-3β-tert-Butyldimethylsilyloxy-chola-5,7-diene-24-carboxylate (10) comprising;

9

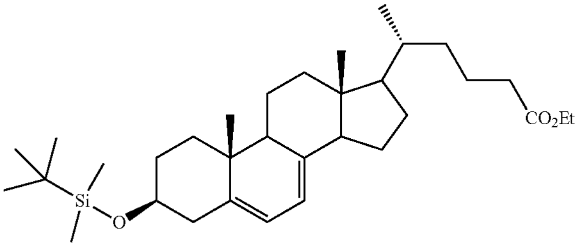

In another aspect, the present invention provides the novel intermediate, 3β-tert-Butyldimethylsilyloxy-25-hydroxy-chola-5,7-diene (11) comprising;

11

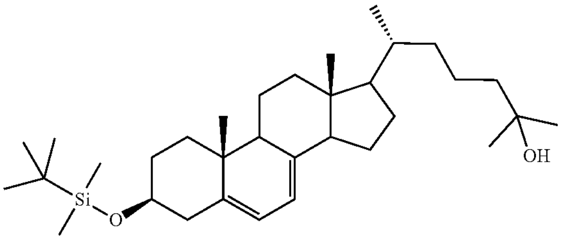

DETAILED DESCRIPTION OF THE INVENTION

The present invention discloses an improved and cost effective process for conversion of Ergosterol to vitamin D3 and its analogue calcifediol of general formula (I);

(I)

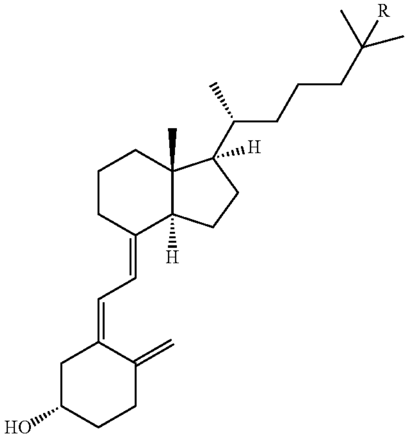

R = H: vitamin D3
R = OH: 25-OH-vitamin D3 (Calcifediol)

via the precursors of general formula (II)

(II)

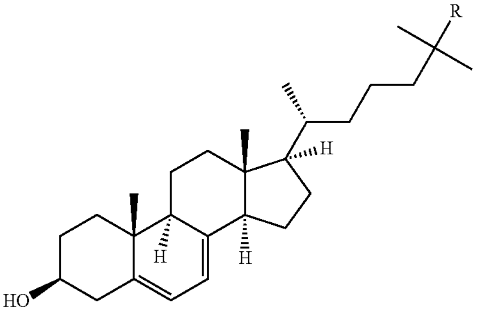

7 or 8
R = H, Provitamin D3 (7)
R-OH, 25-OH provitamin in D3 (8)

which is obtained from the key intermediate viz. 3β-tert-Butyldimethylsilyloxy-22-hydroxy-23,24-bisnorchola-5,7-diene (5).

The known methods for removal of 5,7 diene adduct of C-22 steroid i.e. ergosterol, are either very drastic, require strong basic conditions or give unsatisfactory yields. The present invention provides a mild and smooth reaction for the regeneration of steroidal 5,7 diene from Diels Alder adduct (4) in quantitative yield and high purity, wherein, both the deprotection and reduction of aldehyde to C22-OH is carried out in a single step.

Accordingly, the intermediate 3β-tert-Butyldimethylsilyloxy-22-hydroxy-23,24-bisnorchola-5,7-diene (5) is prepared by deprotecting Diels Alder adduct, 3β-tert-Butyldimethylsilyloxy-5α,8α-(1,4-dioxo-1,2,3,4-tetrahydro-phthalazine-2,3-diyl)-23,24-bisnorchol-6-en-22-al (4) and reducing the aldehyde to 22-OH in one step with $LiAlH_4$ in THF at 45° C. for 3 hours to obtain the said intermediate.

The intermediate 3β-tert-Butyldimethylsilyloxy-5α,8α-(1,4-dioxo-1,2,3,4-tetrahydro-phthalazine-2,3-diyl)-23,24-bisnorchol-6-en-22-al (4) is obtained from ergosterol by known process.

In an embodiment, the present invention discloses an improved, cost effective process for the conversion of ergosterol to vitamin D3 and its analogue, calcifediol of general formula (I)

(I)

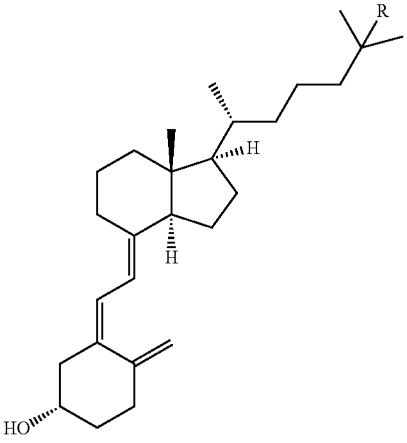

R = H: vitamin D3
R = OH: 25-OH-vitamin D3 (Calcifediol)

via the provitamin precursor of general formula (II)

(II)

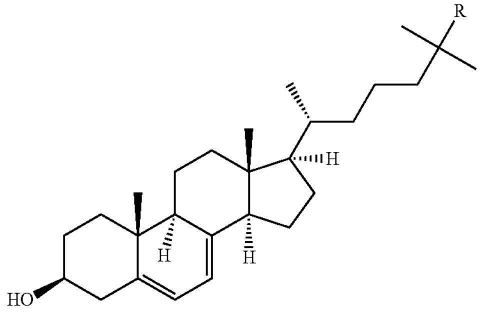

7 or 8

R = H, Provitamin D3 (7)
R—OH, 25-OH provitamin in D3 (8)

which comprises;

i. Converting Ergosterol to Diels Alder adduct, 3β-tert-Butyldimethylsilyloxy-5α,8α-(1,4-dioxo-1,2,3,4-tetrahydro-phthalazine-2,3-diyl)-23,24-bisnorchol-6-en-22-al (4) by known process;

ii. Deprotecting Diels Alder adduct, 3β-tert-Butyldimethylsilyloxy-5α,8α-(1,4-dioxo-1,2,3,4-tetrahydro-phthalazine-2,3-diyl)-23,24-bisnorchol-6-en-22-al (4) and reducing the aldehyde to 22-OH in one step with $LiAlH_4$ to obtain the intermediate 3β-tert-Butyldimethylsilyloxy-22-hydroxy-23,24-bisnorchola-5,7-diene (5);

iii. Tosylating the intermediate (5) of step (i) to obtain the intermediate 3β-tert-Butyldimethylsilyloxy-22-tosyloxy-23,24-bisnorchola-5,7-diene (6);

iv. Converting the intermediate (6) to provitamin precursor of general formula (II); and v. Irradiating the pro-vitamin precursor of formula (II) in presence of photosensitizer to obtain compounds of formula (I) followed by crystallization.

Scheme 1

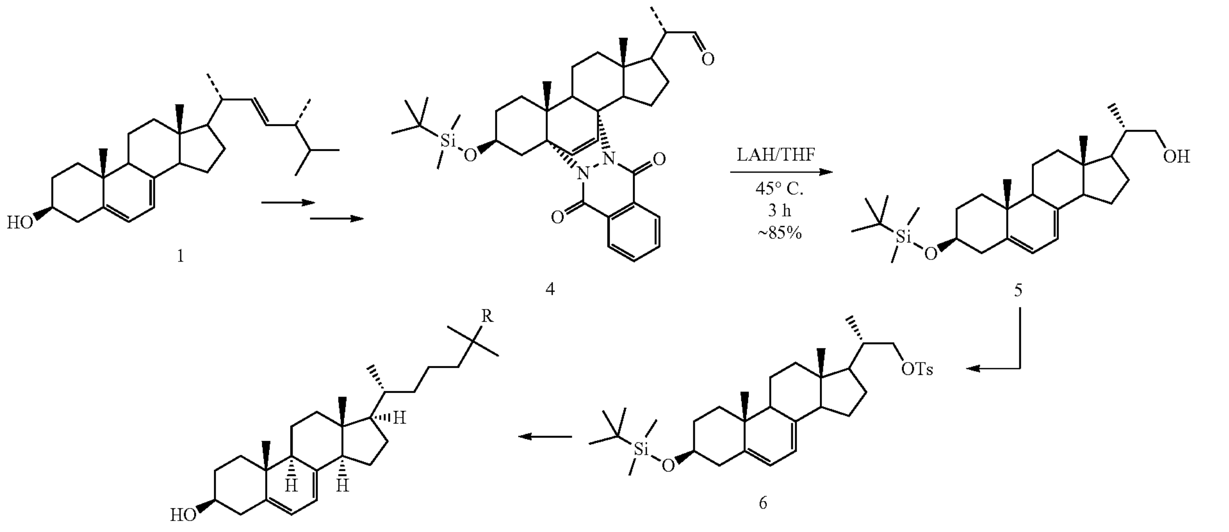

1
4
5
6

(II)

R = H, Provitamin D3
R-OH, 25-OH provitamin in D3

Accordingly, to a solution of lithium aluminium hydride ($LiAlH_4$) solution of the intermediate (4), prepared from ergosterol, was added dropwise at 0° C. under nitrogen atmosphere. The reaction mixture was stirred at 40-45° C. for about 3 hours, quenched in a mixture of solvent and 15% NaOH, filtered, washed, extracted in solvent, dried and concentrated to obtain 3β-tert-Butyldimethylsilyloxy-22-hydroxy-23,24-bisnorchola-5,7-diene (5) as white solid.

To the solution of solid intermediate (5) was added tosyl chloride at 0° C. under nitrogen atmosphere and stirred for about 4 hours at same temperature until TLC indicated completion of reaction. The solid, 3β-tert-Butyldimethylsilyloxy-22-tosyloxy-23,24-bisnorchola-5,7-diene (6), obtained was filtered, washed and dried.

The intermediate (6) formed in the present invention was further reacted with suitable Grignard reagent to obtain the precursors of formula (II) for further conversion to vitamin D3 and its analogue calcifediol of formula (I).

In another embodiment, the present invention provides an improved, cost effective process for the conversion of ergosterol to vitamin D3 and its analogue, calcifediol of Formula (I)

(I)

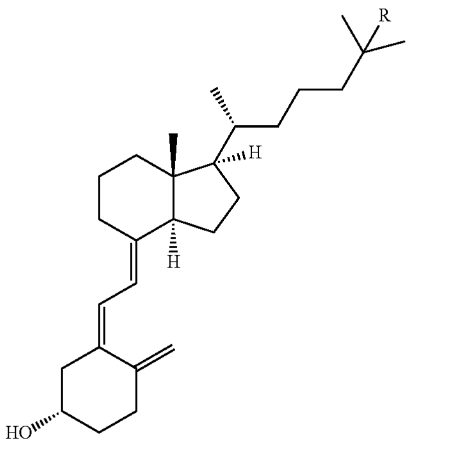

R = H; vitamin D3
R = OH; 25-OH-vitamin in D3 (Calcifediol)

via the provitamin precursor, 7-DHC of formula (IIA),

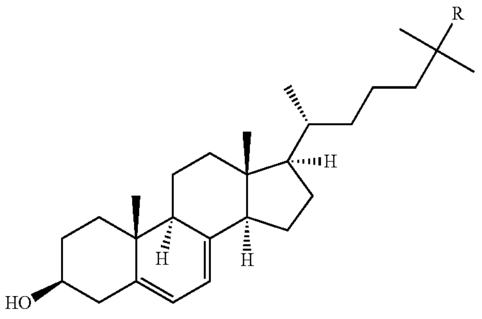

(wherein R=H) comprising;

i. Reacting the intermediate (6) obtained by the process described above with Grignard reagent of 1-Bromo-3-methylbutane in presence of $CuBr{\cdot}Me_2S$ followed by desilylation with TBAF to obtain 7-DHC of Formula (IIA); and
ii. Irradiating 7-DHC (IIA) in presence of photosensitizer to compounds of Formula (I) followed by crystallization.

Scheme 2

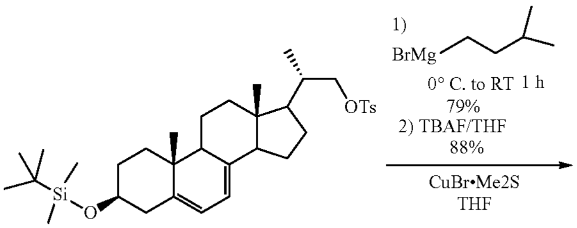

6

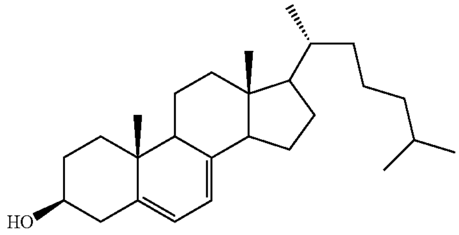

(IIA)
7-DHC

Accordingly, to stirred solution of magnesium turnings were added few drops 1,2-dibromoethane under nitrogen atmosphere followed by addition of few drops 1-bromo-3-methylbutane and the mixture was heated to about 50° C. for few minutes to initiate the reaction. The remaining amount of the solution of 1-bromo-3-methylbutane was added drop wise under nitrogen atmosphere and the mixture was further stirred at about 50° C. for about 30 minutes. The reaction mixture was cooled at 0° C. and a suspension of $CuBr{\cdot}Me_2S$ was added followed by addition of solution of 3β-tert-Butyldimethylsilyloxy-22-tosyloxy-23,24-bisnorchola-5,7-diene (6) at 0° C. under $N_2$. The mixture was stirred at room temperature for 2-3 hours until completion of the reaction. The reaction mixture was poured into saturated aqueous NH4Cl at 0° C. and the aqueous layer was extracted twice in organic solvent. The combined organic layers were washed with saturated aqueous NH4Cl, saturated aqueous $NaHCO_3$ and brine, and dried. The mixture was filtered, concentrated to afford the pale yellow solid of 3β-tert-Butyldimethylsilyloxy-cholesta-5,7-diene, filtered and dried to get white solid which was used as such for next reaction without further purification.

The compound, 3β-tert-Butyldimethylsilyloxy-cholesta-5,7-diene and $Bu_4NF{\cdot}3H_2O$ (TBAF) in solvent were stirred under inert atmosphere at room temperature until completion of the reaction. The reaction mass was washed, the organic phase separated, dried to obtain 7-DHC (IIA) as white solid.

The precursor compound 7-DHC (IIA) was irradiated and thermally treated in presence of photosensitzer to yield vitamin D3 and its analogue calcifediol of formula (I).

In yet another embodiment, the present invention provides an improved, cost effective process for the conversion of ergosterol to vitamin D3 and its analogue, calcifediol of Formula (I)

(I)

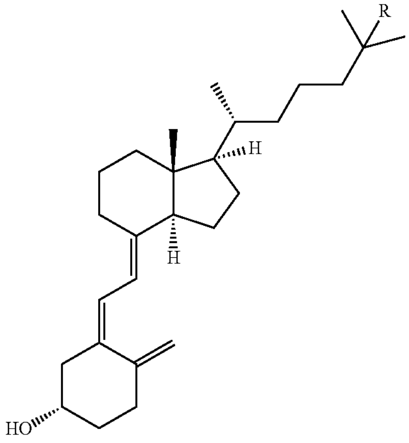

R = H; vitamin D3
R = OH; 25-OH-vitamin D3 (Calcifediol)

via the provitamin precursor, 7-DHC of formula (IIA), (IIA)

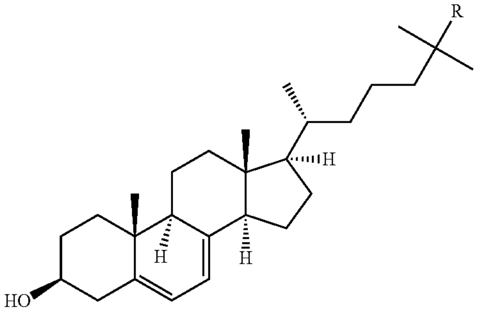

(wherein R=H) comprising;

i. Reacting the intermediate (6) of step (ii) with 4-bromo-2-methyl-2-[(trimethylsilyl)oxy]butane and CuBr·$SMe_2$ followed by desilylation to obtain 25-OH provitamin D3 of formula (IIB); and
ii. Irradiating 25-OH provitamin D3 (IIB) in presence of photosensitizer to obtain compounds of formula (I) followed by crystallization.

Accordingly, to stirred solution of magnesium turnings was added few drops of 1,2-dibromoethane under nitrogen atmosphere followed by addition of few drops of 4-bromo-2-methyl-2-[(trimethylsilyl)oxy]butane and the mixture was heated to about 50° C. for few minutes to initiate reaction. The remaining solution of 4-bromo-2-methyl-2-[(trimethylsilyl)oxy]butane was then added dropwise under $N_2$ and the mixture was stirred at the same temperature for about 30 mins. The reaction mixture was then cooled to 0° C. and a suspension of CuBr·$Me_2S$ was added followed by drop wise addition of solution of 3β-tert-Butyldimethylsilyloxy-22-tosyloxy-23,24-bisnorchola-5,7-diene (6) at 0° C. and under $N_2$. After being stirred at room temperature for 2-3 h, the reaction mixture was poured into saturated aqueous NH4Cl at 0° C. and the aqueous layer was extracted in the solvent. The combined organic layers were washed with saturated aqueous $NH_4Cl$, saturated aqueous $NaHCO_3$ and brine, and dried. The obtained mixture was filtered and concentrated in vacuo. The oily residue was stirred in suitable solvent to afford β-tert-Butyldimethylsilyloxy-25-triethylsilyloxy-cholesta-5,7-diene as white solid, filtered, dried and used as such for next reaction without further purification.

The compound, 3β-tert-Butyldimethylsilyloxy-25-trimethylsilyloxycholesta-5,7-diene and Bu4NF·3H2O in solvent were stirred under argon, washed, separated the organic phase dried to obtain 3β-25-Dihydroxycholesta-5,7-diene (provitamin of 25-Hydroxy vitamin D3 (IIB) as white solid.

The precursor compound 3β-25-Dihydroxycholesta-5,7-diene (provitamin of 25-Hydroxy vitamin D3 (IIB) was irradiated and thermally treated in presence of photosensitzer to yield vitamin D3 and its analogue calcifediol of formula (I).

In another preferred embodiment, the present invention discloses the iodo intermediate, 3β-tert-Butyldimethylsilyloxy-22-iodo-23,24-bisnorchola-5,7-diene (9) for preparation of vitamin D3 and its analogue calcifediol of general formula (I) from ergosterol, comprising;

Scheme 3

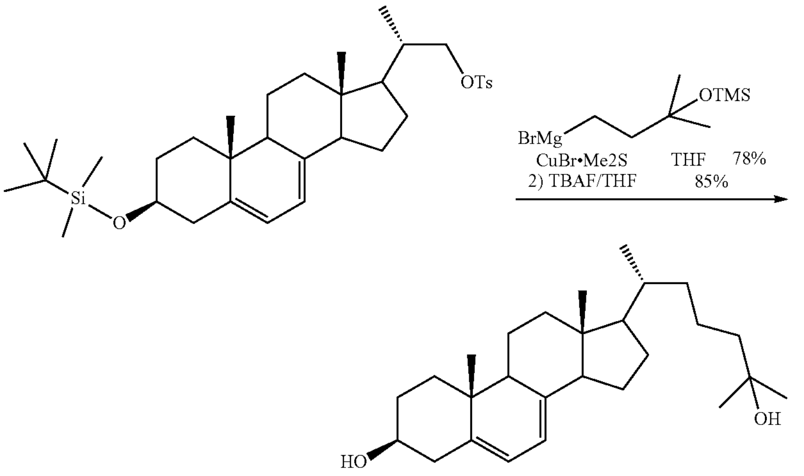

(IIB)

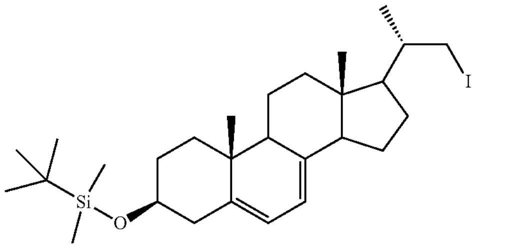

9

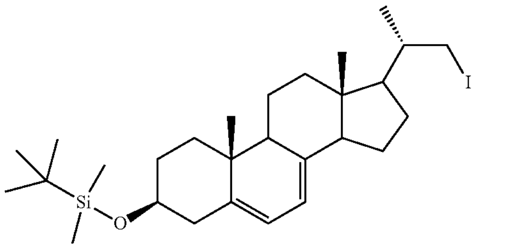

9

In yet another embodiment, the present invention discloses an improved, cost effective process for preparation of vitamin D3 and its analogue, calcifediol of Formula (I)

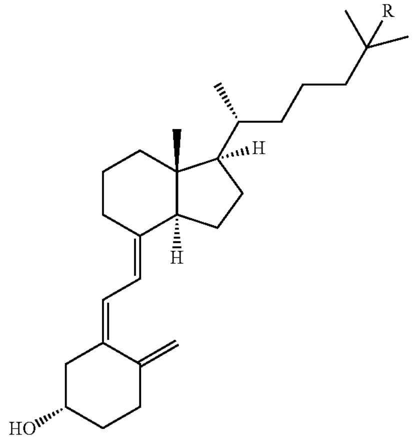

(I)

R = H; vitamin D3

R = OH; 25-OH-vitamin D3 (Calcifediol)

from ergosterol, via the precursor 25-OH provitamin D3 (IIB) comprising;

i. Reacting intermediate 3β-tert-Butyldimethylsilyloxy-22-tosyloxy-23,24-bisnorchola-5,7-diene (6) with NaI/acetone at reflux to obtain the intermediate 3β-tert-Butyldimethylsilyloxy-22-iodo-23,24-bisnorchola-5,7-diene (9);

ii. Alkylating the intermediate (9) with Ni(0) complex derived from ethyl acrylate in-situ to yield the intermediate ester, Ethyl-3β-tert-Butyldimethylsilyloxy-chola-5,7-diene-24-carboxylate (10);

iii. Reacting the ester (10) with Grignard reagent to obtain 3β-tert-Butyldimethylsilyloxy-25-hydroxychola-5,7-diene (11) followed by desilylation to yield 25-OH provitamin D3 (IIB); and iv. Irradiating 25-OH provitamin D3 (IIB) in presence of photosensitizer to obtain compounds of formula (I) followed by crystallization.

Scheme 4

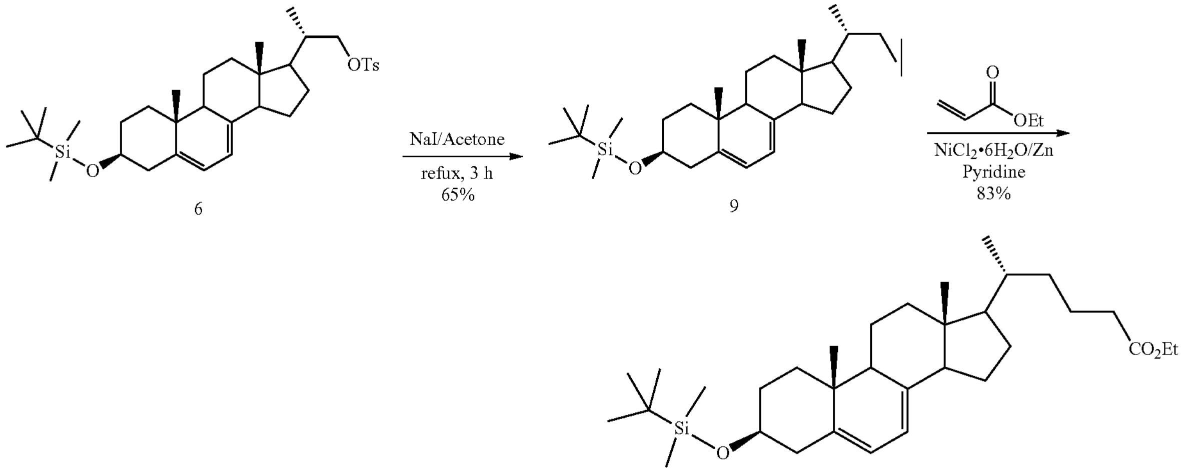

6

9

10

-continued

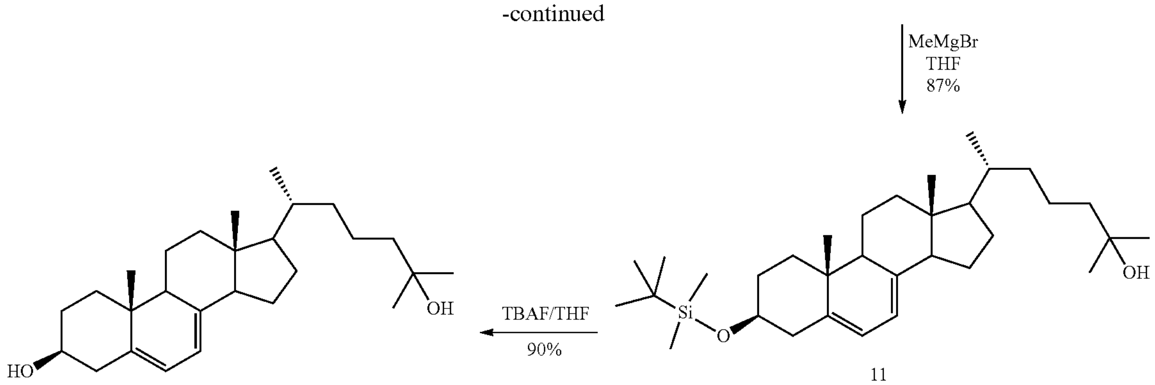

11

(400)

25-OH provitamin D3

Accordingly, to the mixture of 3β-tert-Butyldimethylsilyloxy-22-tosyloxy-23,24-22-bisnorchola-5,7-diene (6) was added sodium iodide and dry acetone and the mixture was heated at reflux for about 3-4 hours and then cooled. The mixture was poured in water and extracted in organic solvent. The organic were further washed and dried, concentrated to obtain 3β-tert-Butyldimethylsilyloxy-22-iodo-23,24-bisnorchola-5,7-diene (9) as white solid.

To a vigorously stirred mixture of zinc dust and ethyl acrylate in solvent was added $NiCl_2 \cdot 6H_2O$. The mixture was heated to about 50° C., whereupon an exotherm ensued, and stirring was continued at about 65° C. for about 30 min. The resulting reddish-brown mixture was cooled to about 25° C. and treated during 0.5 h with a solution of 3β-tert-Butyldimethyl silyloxy-22-iodo-23,24-bisnorchola-5,7-diene (9) at a rate so as to maintain the temperature below 25° C. The mixture was stirred at the same temperature for about 4 h, poured into suitable solvent and filtered. The filtrates were further washed, evaporated, dried to give the ester, ethyl-3β-tert-Butyldimethylsilyloxy-chola-5,7-diene-24-carboxylate (10) as a brownish solid, which was used directly in the next step.

To the stirred, cooled (ice bath) solution of ester (10) in solvent under nitrogen was added methyl magnesium bromide during 30 min. The mixture was stirred at ice bath temperature for about 15 min and at room temperature for 2-3 h, cooled to 0° C., and carefully quenched with saturated $NH_4Cl$. The mixture was extracted in the solvent, washed, dried and evaporated in vacuo to give 3β-tert-Butyldimethylsilyloxy-25-hydroxychola-5,7-diene (11) as crude product. The crude product was further stirred in suitable solvent, filtered, dried to get desired product as a colorless solid. Recrystallization was carried out in suitable solvent to 3β-tert-Butyldimethylsilyloxy-25-hydroxychola-5,7-diene (11) as white crystalline solid.

The compound, 3β-tert-Butyldimethylsilyloxy-25-hydroxychola-5,7-diene (11) and $Bu_4NF \cdot 3H_2O$ in solvent were stirred under inert atmosphere. the product was extracted in suitable solvent washed, dried and recrystallized to obtain 3β-25-Dihydroxycholesta-5,7-diene (provitamin of 25-Hydroxy vitamin D3) (IIB).

The Ni(0) complex used in the present invention is conveniently prepared in-situ, indicated by formation of brick red complex without using any hazardous or expensive chemicals. The present process avoids the use of Lithium naphthalenide of the prior art process which is tedious to prepare and further avoids the additional purification process required in the art which employs Lithium naphthalenide for conversion of iodide to the ester. Further, in the present process no separate esterification step is needed and the ester intermediate (10) can be obtained directly in good yield. Moreover, the present process of conjugation addition of ethyl acrylate to obtain the ester (10) is suitable for large scale production.

Alternately, the present invention provides direct preparation of the iodide intermediate, 3β-tert-Butyldimethylsilyloxy-22-iodo-23,24-bisnorchola-5,7-diene (9) from key intermediate, 3β-tert-Butyldimethylsilyloxy-22-hydroxy-23,24-bisnorchola-5,7-diene (5) which is further converted to the precursor 3β-25-Dihydroxycholesta-5,7-diene (provitamin of 25-Hydroxy vitamin D3) (IIB) and finally to vitamin D3 and its analogue calcifediol of formula (I).

In an embodiment, the present invention provides an improved, cost effective process for preparation of vitamin D3 and its analogue, calcifediol of formula (I)

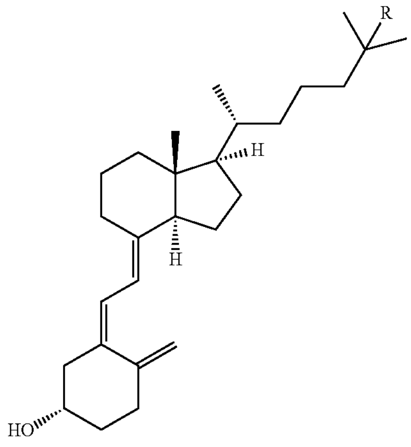

R = H, vitamin D3
R = OH; 25-OH-vitamin D3 (Calcifediol)

from ergosterol, via the precursor 25-OH provitamin D3 (IIB) comprising;

i. Reacting intermediate, 3β-tert-Butyldimethylsilyloxy-22-hydroxy-23,24-bis norchola-5,7-diene (5) with $PPh_3/I_2$ in imidazole to obtain 3β-tert-Butyldimethyl-silyloxy-22-iodo-23,24-bisnorchola-5,7-diene (9);Alkylating the intermediate (9) with Ni(0) complex derived from ethyl acrylate in-situ to yield the intermediate ester, Ethyl-3β-tert-Butyldimethylsilyloxy-chola-5,7-diene-24-carboxylate (10);
ii. Reacting the ester (10) with Grignard reagent to obtain 3β-tert-Butyldimethylsilyloxy-25-hydroxychola-5,7-diene (11) followed by desilylation to yield 25-OH provitamin D3 of formula (IIB); and
iii. Irradiating 25-OH provitamin D3 (IIB) in presence of photosensitizer to obtain compounds of formula (I) followed by crystallization.

Accordingly, the compound (9) of step (i) in Scheme 5, was prepared by adding iodine to a stirred cooled (0° C.) solution of imidazole and triphenyl phosphine in suitable solvent. The mixture was stirred for about 15 min and treated with a solution of 3β-tert-Butyldimethyl silyloxy-22-hydroxy-23,24-bisnorchola-5,7-diene (5) in solvent in a period of about 30 min, keeping the temperature below 10° C. The stirring was continued at 5° C. for about 0.5 h and at room temperature for 2 hrs and the mixture was filtered. The filter cake was washed, dried and evaporated to give a pale yellow semisolid. This was stirred with suitable solvent (to remove most of triphenylphosphine oxide) and the filtrate was evaporated to get compound (9) as white solid.

The intermediate compound (9) obtained was then converted to the precursor 25-OH provitamin D3 (IIB) via formation of the ester intermediate (10) by a process described above.

Scheme 5

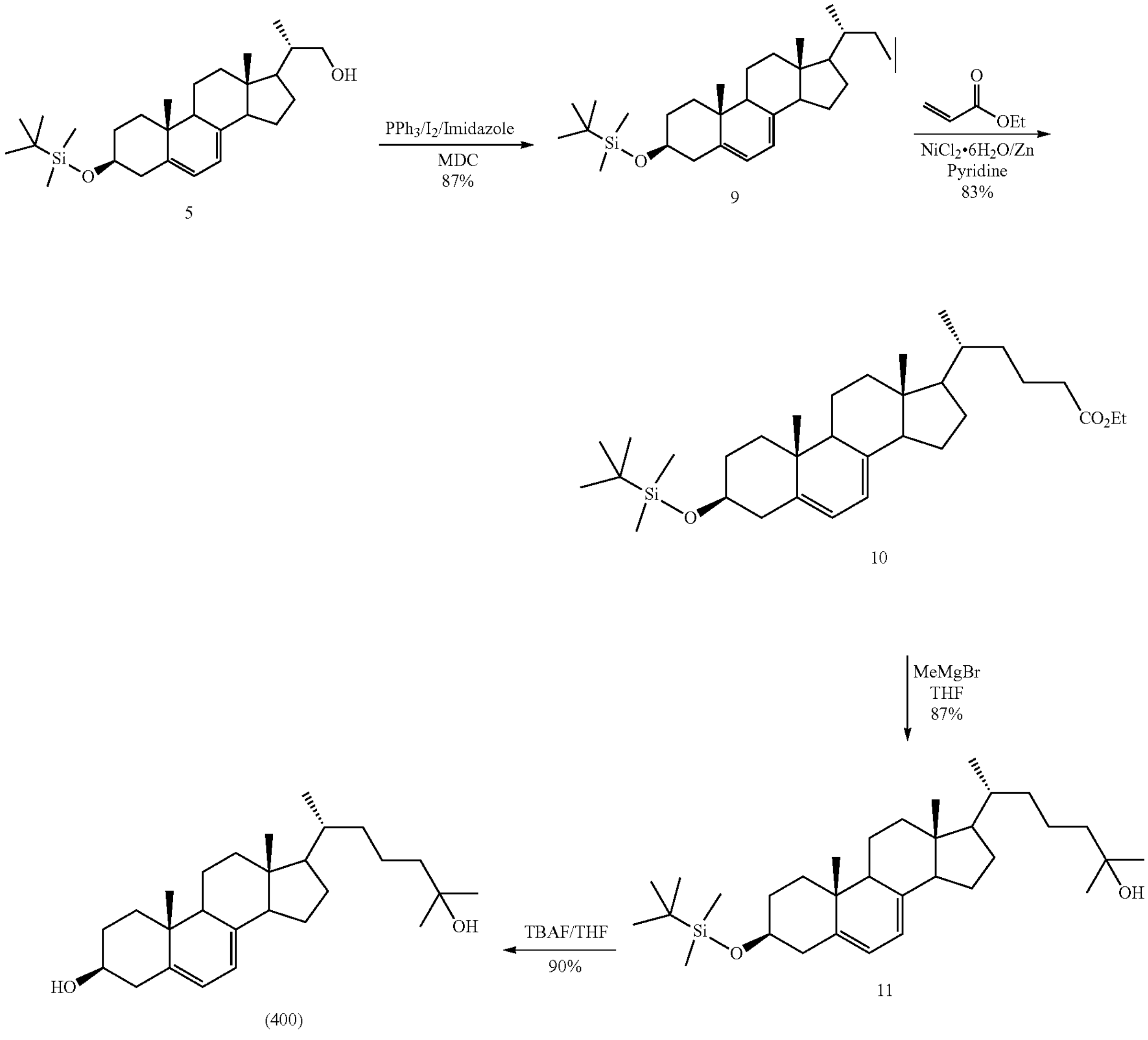

5

9

10

11

(400)

25-OH provitamin D3

In another embodiment, the present invention relates to the intermediate, Ethyl-3β-tert-Butyldimethylsilyloxy-chola-5,7-diene-24-carboxylate (10) comprising;

10

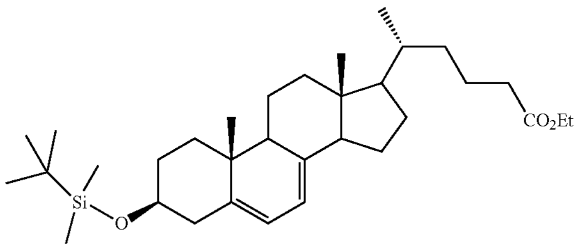

In yet another embodiment, the present invention relates to the intermediate, 3β-tert-Butyldimethylsilyloxy-25-hydroxychola-5,7-diene (11) comprising;

11

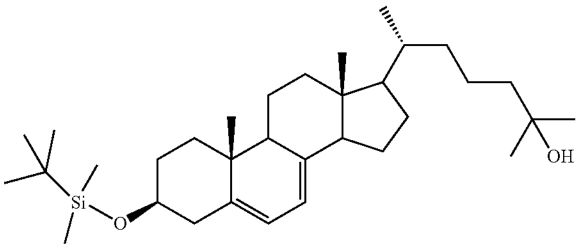

In yet another preferred embodiment, the intermediate compound 3β-tert-Butyldimethyl silyloxy-22-hydroxy-23,24-bisnorchola-5,7-diene (5) useful in the preparation of vitamin D3 and its analogue calcifediol of formula (I) is prepared from ergosterol by a process which comprises;

i. Silylating the 3β-hydroxyl group of ergosterol (1) to obtain the intermediate 3β-tert-Butyldimethylsilyloxy-ergosta-5,7,22-triene (2);
ii. Carrying out the hetero Diels-Alder reaction of intermediate (2) with 1,4-dihydrophthalazine-1,4-dione, prepared in-situ, to obtain the Diels Alder adduct, 3β-tert-Butyldimethylsilyloxy-ergosta-5,7,22-triene-5α,8α-(1,4-dioxo-1,2,3,4-tetrhydro phthalazine-2,3-diyl) ergosta-6,22-diene (3);
iii. Ozonolysis of the adduct (3) to obtain 3β-tert-Butyldimethylsilyloxy-5α,8α-(1,4-dioxo-1,2,3,4-tetrahydro-phthalazine-2,3-diyl)-23,24-bisnorchol-6-en-22-al (4);
iv. Deprotecting Diels Alder adduct, and reducing the 22-aldehyde to 22-OH of 3β-tert-Butyldimethylsilyloxy-5α,8α-(1,4-dioxo-1,2,3,4-tetrahydro-phthalazine-2,3-diyl)-23,24-bisnorchol-6-en-22-al (4) in one step with $LiAlH_4$ to obtain the intermediate 3β-tert-Butyldimethylsilyloxy-22-hydroxy-23,24-bisnorchola-5,7-diene (5).

Scheme 6

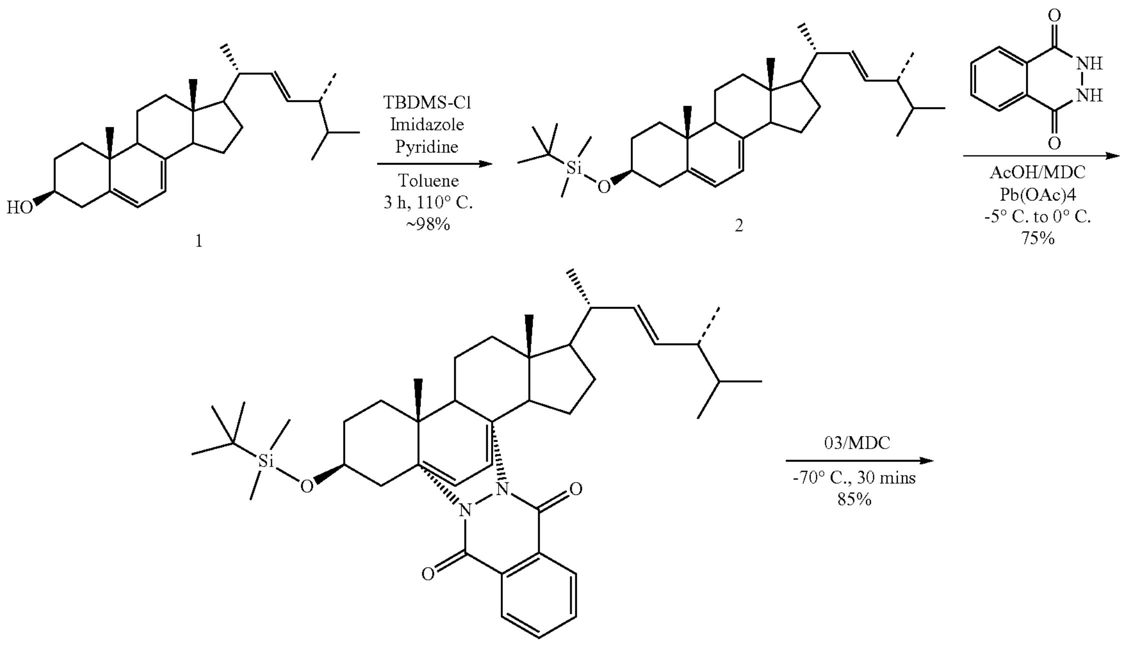

1 2 3

-continued

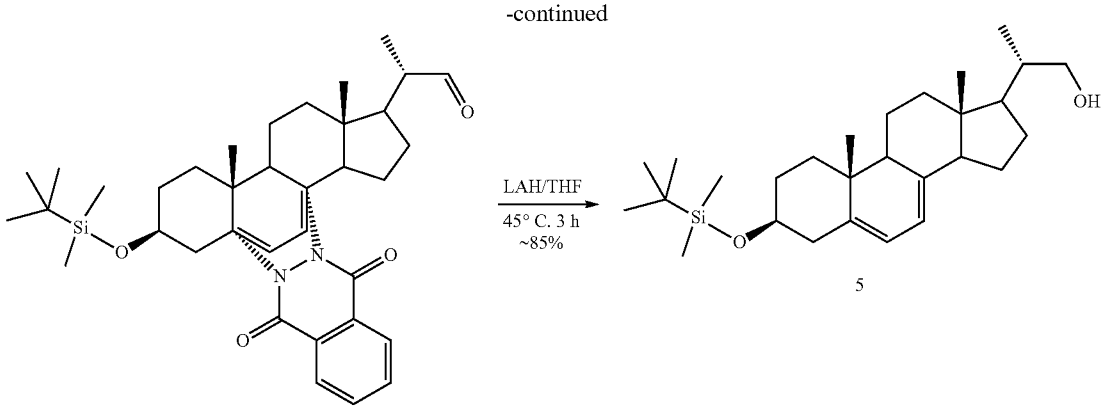

4

5

According to the Scheme 6, Ergosterol (1) was reacted with tert-butyldimethylsilyl chloride (TBDMS-Cl) in solvent mixture at a temperature ranging from 100-120° C. to obtain 3β-tert-Butyldimethylsilyloxy-ergosta-5,7,22-triene (2). To the cooled solution of the intermediate in solvent, phthalhydrazide with Pb(OAc)4 was added dropwise and the reaction was monitored by TLC. After about 2 hours, neutral $Al_2O_3$ was added and the mixture was stirred until yellow solid of adduct 3β-tert-Butyldimethylsilyloxy-ergosta-5,7,22-triene-5α,8α-(1,4-dioxo-1,2,3,4-tetrhydro phthalazine-2,3-diyl) ergosta-6,22-diene (3) was obtained. The product was filtered, washed and dried. The mixture of ozone and oxygen was bubbled through the solution of intermediate (3) at about-70 to −80° C. for about 3 hours. After completion of the reaction, the mixture was concentrated in vaccuo and purified to obtain 3β-tert-Butyldimethylsilyloxy-5α,8α-(1,4-dioxo-1,2,3,4-tetrahydro-phthalazine-2,3-diyl)-23,24-bis-norchol-6-en-22-al (4).

In the preferred embodiment of the process, to a solution of lithium aluminium hydride (LiAlH4) solution of the intermediate (4) obtained was added dropwise at 0° C. under nitrogen atmosphere. The reaction mixture was stirred at 40-45° C. for about 3 hours, quenched in a mixture of solvent and 15% NaOH, filtered, washed, extracted in solvent, dried and concentrated to obtain 3β-tert-Butyldimethylsilyloxy-22-hydroxy-23,24-bisnorchola-5,7-diene (5) as white solid. In an embodiment, the solvents used in the process steps of the present invention is selected from polar, non-polar; protic or aprotic solvents such as C1-C6 alcohols; ethers such as THF, diethyl ether; ketones, DMF, DMSO, halogenated hydrocarbons, C1-C7 straight or branched hydrocarbons, esters, acetonitrile and such like alone or mixtures thereof.

The temperature employed in the present invention ranges from low temperature of about −80° C. to high temperature of about 120° C. depending on the type of reaction performed.

In another preferred embodiment, the precursors of vitamin D3 of general formula (II) obtained by the process of the present invention described above is converted to vitamin D3 and its analogue calcifediol by irradiation in presence of sensitizer and thermal reaction.

Accordingly, the process for preparation of vitamin D3 and its analogue calcifediol from 7-DHC and 25-OH provitamin D3 of general formula (II) with reduced impurities comprising:

i. irradiating 7-DHC and/or 25-OH provitamin D3 obtained by the present process from ergosterol, an antioxidant and solvent in presence of the photosensitizer under medium pressure mercury lamp as light source;
ii. concentrating the irradiated solution of step (i), cooling and crystallizing out the unreacted mass;
iii. filtering and washing the unreacted mass of step (i) and reused for irradiation;
iv. evaporating the filtrate under vacuum to obtain crude product, dissolving the crude product in solvent, refluxing, concentrating under vacuum to obtain reddish orange mass followed by purifying;
v. repeating the step (iv) of concentration of the filtrate severally to obtain quantitative yield of the pure product.

The present photochemical process may be conducted in any reactor suitable for Photo reactions. The reactor design is not critical for the present invention. For example, the 25-OH-7-dehydrocholesterol may be irradiated in a falling-film reactor, especially suitable for production of previtamin D on an industrial scale. However, it is also possible to irradiate very small amounts of the 25-OH-7-dehydrocholesterol in a micro reactor. The use of a micro reactor in combination with a mercury lamp enables production of small quantities of previtamin D.

The irradiation is performed in the solvent that does not absorb or has low absorbency for UV irradiation above 240 run and sufficiently dissolves the 25-OH-7-dehydrocholesterol or the derivative of interest can be used. Examples include lower alcohols such as methanol, ethanol and 1-propanol: simple ethers, such as diethylether; cyclic ethers, such as tetrahydrofuran and 1,4-dioxane: unsymmetrical ethers, such as tert-butyl methyl ether; alkanes, such as n-hexane, and mixtures thereof; preferably the solvent is THF.

Typically, the concentration of the 25-OH-7-dehydrocholesterol, in the solvent is within the range of from 1 to 10% by weight, preferably from 3 to 10% by weight.

The irradiation temperature does not affect the photochemical reaction. Generally, the temperature is selected to provide solubility of the 25-OH-7-dehydrocholesterol in the solvent employed. Depending on the type of solvent and specific 25-OH-7-dehydrocholesterol employed, the irradiation is typically performed at a temperature within the range of from −20 to 60° C., preferably form 0 to 50° C., more preferably from 10 to 45° C., and most preferably from 25 to 45° C.

The irradiation may be performed in the presence of a free radical scavenger, e.g. tert-butyl hydroxy anisole (BHA), and sensitizers, such as anthracene,3-acetylanthracene and 5-(3-pyridyl)-2,2'-bithiophene, preferably 5-(3-pyridyl)-2,2'-bithiophene to minimize degradation of previtamin D and formation of unwanted byproducts tachysterol and lumisterol. The use of the sensitizer 5-(3-pyridyl)-2,2'-bithiophene for photo irradiation is described in the Applicants earlier filed patent application No. 201921021829.

During photo irradiation, in the case of 25-OHprevitamin D3 preparation, 25-OH 7-DHC, previtamin D3 and the unwanted by products lumisterol and tachysterol form a photochemical equilibrium. It is evident that even at high conversion of 7-DHC the theoretical selectivity for previtamin D is still relatively high (>50%) at a wavelength of 282 nm whereas tachysterol will become the main product at high conversion of 25-OH7-DHC at a wavelength of 254 nm. It is thus a significant advantage of the present process that a mercury lamp having the matching wavelength to favour the production of previtamin D3 even at high conversion, can be employed. Nevertheless, it may be preferred to conduct the present process at very low conversion of 25-OH7-DHC, e.g. not more than 5%, in order to obtain a very high selectivity for previtamin D3, e.g. at least 96%. Slightly higher conversions will result in slightly lower, though still high selectivities for previtamin D3, e.g. a 25-OH7-DHC conversion of not more than 6% results in a previtamin D3 selectivity of at least 95% and a 25-OH7-DHC conversion of not more than 7% results in a previtamin D3 selectivity of at least 94%. It is within the ordinary skill of the expert involved to decide whether the process should be conducted at high or low conversion.

In another embodiment, the present invention discloses a process for preparation of 25-OH vitamin D3 by thermal rearrangement of 25-OH previtamin D3. The thermal conversion to the 25-OH vitamin D3 is a sigmatropic 1,7-hydrogen shift from C-19 to C-9 and is done at a suitable point in the process after the photochemical reaction.

The thermal conversion in the present invention is performed before or after the separation of the 25-OH-7-dehydrosterol to avoid formation of undesired impurities/byproducts.

Scheme 7

Reaction 1:

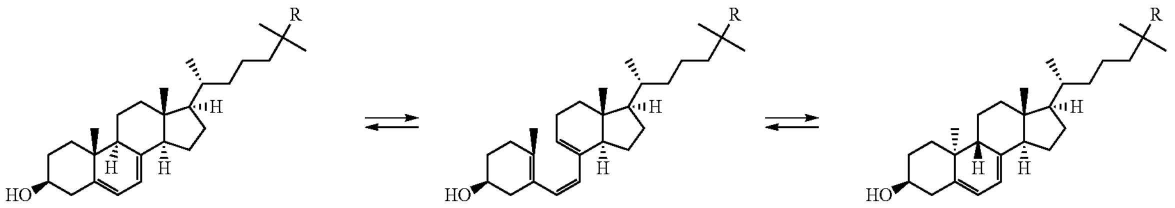

7 or 8 12 13 Lumisteral

R = H, Provitamin D3 (7)
R—O H, 25-OH provitamin D3 (8)

Pre vitamin D3

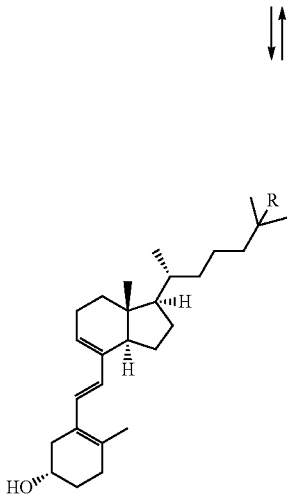

14
tachysterol

-continued

Reaction 2:

Previtamin D3
R = H, OH

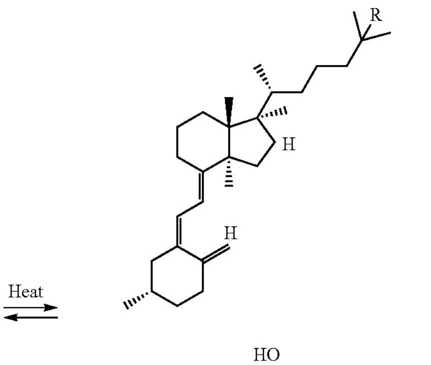

R = H: vitamin D3
R = OH: 25-OH-vitamin D3 (Calcifediol)

In an embodiment, the present invention relates to an improved, cost effective process for synthesis of vitamin D3 or its analogue calcifediol from ergosterol comprising;

i. Silylating the 3β-hydroxyl group of ergosterol (1) to obtain the intermediate 3β-tert-Butyldimethylsilyloxy-ergosta-5,7,22-triene (2);
ii. Carrying the hetero Diels-Alder reaction of intermediate (2) with 1,4-dihydrophthalazine-1,4-dione, prepared in-situ to obtain the Diels Alder adduct, 3β-tert-Butyldimethylsilyloxy-ergosta-5,7,22-triene-5α,8α-(1,4-dioxo-1,2,3,4-tetrhydro phthalazine-2,3-diyl) ergosta-6,22-diene (3);
iii. Ozonolysis of the adduct (3) to obtain 3β-tert-Butyldimethylsilyloxy-5α,8α-(1,4-dioxo-1,2,3,4-tetrahydro-phthalazine-2,3-diyl)-23,24-bisnorchol-6-en-22-al (4);
iv. Deprotecting Diels Alder adduct, and reducing the 22-aldehyde to 22-OH of 3β-tert-Butyldimethylsilyloxy-5α,8α-(1,4-dioxo-1,2,3,4-tetrahydro-phthalazine-2,3-diyl)-23,24-bisnorchol-6-en-22-al (4) in one step with $LiAlH_4$ to obtain the intermediate 3β-tert-Butyldimethylsilyloxy-22-hydroxy-23,24-bisnorchola-5,7-diene (5);
v. Tosylating the intermediate (5) of step (i) to obtain the intermediate 3β-tert-Butyldimethylsilyloxy-22-tosyloxy-23,24-bisnorchola-5,7-diene (6);
vi. Reacting the intermediate (6) of step (ii) with Grignard reagent of 1-Bromo-3-methylbutane or 4-bromo-2-methyl-2-[(trimethylsilyl)oxy]butane and $CuBr{\cdot}SMe_2$ followed by desilylation to obtain 7-DHC (formula IIA) or 25-OH pro-vitamin D3 (formula IIB); and
vii. irradiating the precursors (IIA) and/or (IIB) of step (vi) in presence of an antioxidant, solvent and photosensitizer 5-(3-pyridyl)-2,2'-bithiophene under medium pressure mercury lamp as light source to obtain vitamin D3 and its analogue calcifediol.

In another aspect, the present invention relates to an improved, cost effective process for synthesis of vitamin D3 or its analogue calcifediol from ergosterol comprising:

i. Silylating the 3β-hydroxyl group of ergosterol to obtain the intermediate 3β-tert-Butyldimethylsilyloxy-ergosta-5,7,22-triene (2);
ii. Carrying the hetero Diels-Alder reaction of intermediate (2) with 1,4-dihydrophthalazine-1,4-dione, prepared in-situ to obtain the Diels Alder adduct, 3β-tert-Butyldimethylsilyloxy-ergosta-5,7,22-triene-5α,8α-(1,4-dioxo-1,2,3,4-tetrhydro phthalazine-2,3-diyl) ergosta-6,22-diene (3);
iii. Ozonolysis of the adduct (3) to obtain 3β-tert-Butyldimethylsilyloxy-5α,8α-(1,4-dioxo-1,2,3,4-tetrahydro-phthalazine-2,3-diyl)-23,24-bisnorchol-6-en-22-al (4);
iv. Deprotecting Diels Alder adduct, and reducing the 22-aldehyde to 22-OH of 3β-tert-Butyldimethylsilyloxy-5α,8α-(1,4-dioxo-1,2,3,4-tetrahydro-phthalazine-2,3-diyl)-23,24-bisnorchol-6-en-22-al (4) in one step with $LiAlH_4$ to obtain the intermediate 3β-tert-Butyldimethylsilyloxy-22-hydroxy-23,24-bisnorchola-5,7-diene (5);
v. Tosylating the intermediate (5) of step (i) to obtain the intermediate 3β-tert-Butyldimethylsilyloxy-22-tosyloxy-23,24-bisnorchola-5,7-diene (6);
vi. Reacting intermediate 3β-tert-Butyldimethylsilyloxy-22-tosyloxy-23,24-bisnorchola-5,7-diene (6) with NaI/acetone at reflux to obtain the intermediate 3β-tert-Butyldimethylsilyloxy-22-iodo-23,24-bisnorchola-5,7-diene (9);
vii. Alkylating the intermediate (9) with Ni(0) complex derived from ethyl acrylate in-situ to yield the intermediate ester, Ethyl-3β-tert-Butyldimethylsilyloxy-chola-5,7-diene-24-carboxylate (10);
viii. Reacting the ester (10) with Grignard reagent to obtain 3β-tert-Butyldimethylsilyloxy-25-hydroxy-chola-5,7-diene (11) followed by desilylation to yield 25-OH provitamin D3 (IIB); and
ix. irradiating the precursors (IIB) of step (viii) in presence of an antioxidant, solvent and photosensitizer 5-(3-pyridyl)-2,2'-bithiophene under medium pressure mercury lamp as light source to obtain vitamin D3 and its analogue calcifediol.

Alternately, the intermediate 3β-tert-Butyldimethylsilyloxy-22-iodo-23,24-bisnorchola-5,7-diene (9) may be obtained by direct iodination of 3β-tert-Butyldimethylsilyloxy-22-hydroxy-23,24-bisnorchola-5,7-diene (5) with $PPh_3$ in imidazole.

The present invention provides a process for preparation of vitamin D3 and its analogue calcifediol in quantitative yield and purity which is safe, economical and industrially viable. The vitamin D3 and its analogue is obtained which is of pharmaceutical grade and can safely be consumed by humans.

The present invention is further illustrated by the following example which is provided merely to be exemplary of the invention and do not limit scope of the invention.

Example 1: 3β-tert-Butyldimethylsilyloxy-ergosta-5,7,22-triene (2)

To a stirred solution of Ergosterol (100 g, 0.25 mol) in toluene (600 ml), dry pyridine (80 mL), imidazole (68 g, 1 mol) and t-butyl dimethyl silyl chloride (75.4 g, 0.5 mol) were added at 0° C. under nitrogen. Reaction mixture was stirred at 110° C. for 3 hrs. The reaction was monitored by TLC (heptane/EtOAc, 90:10).

Reaction mass was poured in to ice cold $H_2O$ (5000 mL), the solid material obtained was filtered off, washed with $H_2O$ and MeOH and dried over $Na_2SO_4$. The crude product was crystallized in MeOH.

Analytical Data: Yield: 125 g (98%) Appearance: White solid. M.Pt: 149-151° C. [α]D−75° (c=1.00). GC: 98% (RT: 17.44)

Example 2: 3β-tert-Butyldimethylsilyloxy-ergosta-5,7,22-triene-5α,8α-(1,4-dioxo-1,2,3,4-tetrhydro phthalazine-2,3-diyl) ergosta-6,22-diene (3)

To a cooled solution (0 to −5° C.) of 3β-tert-Butyldimethylsilyloxy-ergosta-5,7,22-triene (2) (125 g, 0.24 mol), of example 1, in $CH_2Cl_2$ (1500 mL) phthalhydrazide (125 g, 0.77 mol), solution of Pb(OAc)4 (191 g, 0.43 mol) in acetic acid (HOAc) (700 mL) were added drop wise for 30 min. The reaction was monitored by TLC (heptane/EtOAc, 9:1). After 2 hours neutral $Al_2O_3$ (500 g) was added and the mixture was stirred at 0° C. for a further 1 h. The yellow solid product was filtered off and washed with $CH_2Cl_2$. The organic layer was separated and washed with aq sat. $NaHCO_3$ and $H_2O$. The solution was dried over $Na_2SO_4$ and the solvent was removed under reduced pressure. To the crude product methanol (1000 mL) was added and extracted with n-heptane (1000 mL×5) and finally combined n-heptane layer was back washed with methanol to remove traces of polar impurities. The n-heptane layer was further washed with saturated salt solution (1000 mL). Removal of n-heptane afforded compound 3 as a yellow amorphous solid.

Analytical Data: Yield: 123.3 g (75%) Appearance: Yellow amorphous solid M.Pt: 106-110° C. [α]D−130° (c=1.00, $CH_2Cl_2$) GC: 72.19% (RT: 17.31)

Example 3: 3β-tert-Butyldimethylsilyloxy-5α,8α-(1,4-dioxo-1,2,3,4-tetrahydro-phthalazine-2,3-diyl)-23,24-bisnorchol-6-en-22-al (4)

A mixture of 03 and 02 was bubbled through the solution of 3β-tert-butyldimethylsilyloxy-5α,8α-(1,4-dioxo-1,2,3,4-tetrahydrophthalazine-2,3-diyl) ergosta-6,22-diene (123 g, 0.179 mol), (3) of example 2, in $CH_2Cl_2$ (2000 mL) and pyridine (250 mL) at −78° C. for 3 h. The mixture was concentrated in vacuo. The residue was purified by heptane treatment to give 3β-tert-butyldimethylsilyloxy-5α,8α-(1,4-dioxo-1,2,3,4-tetrahydro-phthalazine-2,3-diyl)-23,24-bis norchol-6-en-22-al 4 (93.5 g, 85%) as a yellow amorphous solid.

Analytical Data: Yield: 93.5 g (85%) Appearance: Yellow amorphous solid. M.Pt: 110-115° C. [α]D−101° (c=1.00, $CHCl_3$).

Example 4: 3β-tert-Butyldimethylsilyloxy-22-hydroxy-23,24-bisnorchola-5,7-diene (5)

To a solution of $LiAlH_4$ (57 g, 1.5 mol) in THF (500 mL), solution of 3β-tert-butyldimethylsilyloxy-5α,8α-(1,4-dioxo-1,2,3,4-tetrahydro-phthalazine-2,3-diyl)-23,24-bis norchol-6-en-22-al (4) (93 g, 0.15 mol), of example 3, in THF (1000 mL) was added drop wise at 0° C. under nitrogen. After being stirred at 45° C. for 3.0 h, the reaction mixture was quenched with moist THF (57 mL, $H_2O$:THF) at 0° C. followed by addition of 15% NaOH (57 mL) and water (200 mL) and the mixture was stirred for further 1 h. The reaction mass was filtered over celite bed. Washed the celite bed with EtOAc (250 mL×2). The combined organic layer was extracted with water and then washed with brine, dried over $Na_2SO_4$, filtered and concentrated under vacuo to obtain 3β-tert-butyldimethylsilyloxy-22-hydroxy-23,24-bis norchola-5,7-diene as a white solid.

Analytical Data: Yield: 58.4 g (85%) Appearance: White solid. M.pt: 143-146° C. [α]D−81° (c=0.5, $CH_2Cl_2$). GC: 92.40% (RT: 10.88)

Example 5: 3β-tert-Butyldimethylsilyloxy-22-tosyloxy-23,24-bisnorchola-5,7-diene (6)

Tosyl chloride (89 g, 0.46 mol) was added to a stirred solution of 3β-tert-butyldimethylsilyloxy-22-hydroxy-23,24-bis norchola-5,7-diene (5) (58 g, 0.130 mol), of example 4, in pyridine (800 mL) under nitrogen at 0° C. The mixture was stirred for 4 h at this temperature. Reaction was monitored by TLC, with heptane/EtOAc (9:1), the reaction mixture was poured onto crushed ice (4 kg), the solid precipitated was filtered, washed with cold water thoroughly and suck dried. The solid was stirred with methanol. White solid obtained was filtered off and washed with MeOH and dried under vacuo to obtain 3β-tert-Butyldimethylsilyloxy-22-tosyloxy-23,24-bisnorchola-5,7-diene (6).

Analytical Data: Yield: 71 g (92%) M.Pt: 160-162° C. [α]D−62° (c=0.5, EtOAc) GC: 87% (RT: 6.21)

Example 6: 7-dehydrocholesterol (DHC) (IIA)

(A): To stirred magnesium turnings (7.7 g, 0.82 mol) in 50 ml THF, few drops of 1,2-dibromoethane were added under nitrogen atmosphere followed by few drops of 1-bromo-3-methylbutane and heated to 50° C. for few minutes to initiate reaction. This was followed by addition of remaining solution of 1-bromo-3-methylbutane (39 g, 0.25 mol) in THF (50 mL) drop wise under $N_2$. After being stirred at the same temperature i.e. 50° C. for 30 min, the reaction mixture was cooled at 0° C. and a suspension of CuBr·$Me_2S$ (0.18 g, 0.0008 mol) was added followed by drop wise addition of the solution of 3β-tert-Butyldimethylsilyloxy-22-tosyloxy-23,24-bisnorchola-5,7-diene (6) (10 g, 0.0163 mol, 1.0 eq.), of example 5, in THF (100 mL) at 0° C. under $N_2$. After being stirred at room temperature for 2-3 hrs, the reaction mixture was poured into saturated aqueous $NH_4Cl$ at 0° C. and the aqueous layer was extracted twice with EtOAc. The combined organic layer was washed with saturated aqueous $NH_4Cl$, saturated aqueous $NaHCO_3$ and brine, and dried over $MgSO_4$. The obtained mixture was filtered and concentrated in vacuo. The residue was stirred in methanol to afford pale yellow solid of 3β-tert-Butyldimethylsilyloxy-cholesta-5,7-diene, filtered and dried to get a white solid which was used as such for next reaction without further purification.

Analytical Data: Yield: 6.59 g (79%) Appearance: White solid. GC: 96.75% (RT: 14.43)

(B): The compound, 3β-tert-Butyldimethylsilyloxy-cholesta-5,7-diene (6.59 g, 0.0107 mol), obtained in example 6A, and $Bu_4NF·3H2O$ (14 g, 0.053 mol) in THF (250 mL) were stirred under argon atmosphere at room temperature for 2.5 h. EtOAc (250 mL) was then added and the mixture was washed with brine (100×2 mL). The organic phase was separated, dried over $Na_2SO_4$ and the solvent was removed under reduced pressure. The residue was crystallized from MeOH to yield 7-DHC as white solid.

Analytical Data: Yield: 3.7 g (88%) M.Pt: 148-152° C. HPLC: 96.5% (RT: 11.13) GC: 97.71% (RT: 7.41)

$^1$H-NMR: (400 MHz, $CDCl_3$): δ=0.60 (s, 3H), 0.94 (s, 3H), 0.96 (d, 3H), 1.19 (s, 6H), 3.66 (m, 1H), 5.39 (d, 1H), 5.55 (d, 1H).

$^{13}$C-NMR (100 MHz, $CDCl_3$): δ 141.4, 139.7, 119.6, 116.2, 70.4, 55.9, 54.5, 46.2, 42.9, 40.7, 39.5, 39.2, 38.3, 37.0, 36.1, 36.1, 31.9, 28.0, 28.0, 23.8, 23.0, 22.8, 22.5, 21.1, 18.5, 16.2; 11.8.

Example 7: 3β-25-Dihydroxycholesta-5,7-diene (provitamin of 25-Hydroxy vitamin D3) (IIB)

(A): To stirred magnesium turnings (4.0 g, 0.163 mol, 10 eq.) in THF (50 ml) few drops of 1,2-dibromoethane were added under nitrogen atmosphere followed by few drops of 4-bromo-2-methyl-2-[(trimethylsilyl)oxy]butane and heated to 50° C. for few minutes to initiate the reaction. This was followed by addition of remaining solution of 4-bromo-2-methyl-2-[(trimethylsilyl)oxy]butane (38.5 g, 0.163 mol) in THF (50 mL) drop wise under $N_2$ atmosphere. After being stirred at the same temperature i.e. 50° C. for 30 min, the reaction mixture was cooled at 0° C. and a suspension of $CuBr{\cdot}Me_2S$ (3.34 g, 0.0163 mol, 1.0 eq.) in THF (10 ml) was added followed by dropwise addition of solution of 3β-tert-Butyldimethylsilyloxy-22-tosyloxy-23,24-bisnorchola-5,7-diene (6) (10 g, 0.0163 mol, 1.0 eq.), obtained in example 6A, in THF (100 mL) at 0° C. under $N_2$. After being stirred at room temperature for 2-3 h, the reaction mixture was poured into saturated aqueous $NH_4Cl$ at 0° C. and the aqueous layer was extracted twice with ethyl acetate (EtOAc). The combined organic layer was washed with saturated aqueous $NH_4Cl$, saturated aqueous $NaHCO_3$ and brine, and dried over $MgSO_4$. The obtained mixture was filtered and concentrated in vacuo. The oily residue was stirred in acetone to afford β-tert-Butyldimethylsilyloxy-25-triethylsilyloxycholesta-5,7-diene as white solid, filtered and dried and used as such for next reaction without further purification.

Analytical Data: Yield: 8.16 g (78%) Appearance: White solid M.Pt: 116-118° C. GC: 93.8% (RT: 25.86)

(B): Compound, 3β-tert-Butyldimethylsilyloxy-25-trimethylsilyloxycholesta-5,7-diene (8.16 g, 0.0127 mol) of example 7A and $Bu_4NF{\cdot}3H_2O$ (25 g, 0.079 mol) in THF (250 mL) were stirred under argon atmosphere at 40° C. for 4 h. EtOAc (500 mL) was then added and the mixture washed with brine (100×3 mL). The organic phase was separated, dried over $Na_2SO_4$ and the solvent removed under reduced pressure. The residue was crystallized from MeOH.

Analytical Data: Yield: 4.5 g (85%) Appearance: White solid M.Pt: 155-157° C. GC: 97.96% (RT: 10.05)

$^1$H-NMR (400 MHz, $CDCl_3$): δ=0.60 (s, 3H), 0.94 (s, 3H), 0.96 (d, 3H), 1.19 (s, 6H), 3.66 (m, 1H), 5.39 (d, 1H), 5.55 (d, 1H).

The $^1$H NMR data correspond to those known from the literature.

$^{13}$C-NMR: (100 MHz, $CDCl_3$): δ 141.3, 139.8, 119.5, 116.3, 71.1, 70.4, 55.8, 54.4, 46.2, 44.4, 42.9, 40.8, 39.1, 38.3, 37.0, 36.3, 36.0, 32.0, 29.3, 29.2, 28.1, 23.0, 21.1, 20.8, 18.8, 16.3, 11.8.

Example 8a: 3β-tert-Butyldimethylsilyloxy-22-iodo-23,24-bisnorchola-5,7-diene (9)

A mixture of 10 g (0.0167 mole) of 3β-tert-Butyldimethylsilyloxy-22-tosyloxy-23,24-22-bisnorchola-5,7-diene (6), of example 5, sodium iodide (5.0 g, 0.0334 mole) and 200 mL of dry acetone were heated at reflux for 3 hrs and cooled. The mixture was poured in to water and extracted with ethyl acetate. The ethyl acetate extract was washed with 2% sodium thiosulfate solution (100 mL) followed by washing with water, brine solution and finally the ethyl acetate extract was dried over anhydrous sodium sulfate. The extract was concentrated to yield 3β-tert-Butyldimethylsilyloxy-22-iodo-23,24-bisnorchola-5,7-diene as white solid.

Analytical data: Yield: 8.0 g (87%) Appearance: White coloured solid M.pt: 140-142° C. GC analysis: ~95% (RT: 19.5)

Example 8b: 3β-tert-Butyldimethylsilyloxy-22-iodo-23,24-bisnorchola-5,7-diene (9)

Iodine (5.8 g, 0.046 mole) was added to a stirred, cooled (0° C.) solution of 9.4 g (0.138 mole) of imidazole and 12.0 g (0.046 mole) of triphenylphosphine in 100 ml of $CH_2Cl_2$. The mixture was stirred for 15 min and treated with a solution of 3β-tert-Butyldimethylsilyloxy-22-hydroxy-23,24-bisnorchola-5,7-diene (5) (10.0 g, 0.023 mole) of example 4 in 50 mL of $CH_2Cl_2$ during 30 min, keeping the temperature below 10° C. Stirring was continued at 5° C. for 0.5 h and at room temperature for 2 hrs and the mixture was filtered. The filter cake was washed with 100 mL of $CH_2Cl_2$ and combined filtrate and washings were washed with 100 mL of 2% sodium thiosulfate, 100 mL of 0.1N HCl and 300 mL of brine, dried over anhy $Na_2SO_4$ and evaporated to give a pale yellow semisolid. The semisolid was stirred with diethyl ether (to remove most of triphenylphosphine oxide) and the filtrate was evaporated to get 3β-tert-Butyldimethylsilyloxy-22-iodo-23,24-bisnorchola-5,7-diene (9) as white solid.

Analytical data: Yield: 11.0 g (87%) Appearance: White solid M.Pt: 141-143° C. GC analysis: ~95% (19.5)

Example 9: Ethyl-3β-tert-Butyldimethylsilyloxy-chola-5,7-diene-24-carboxylate (10)

To a vigorously stirred mixture of 4.68 g (0.072 mole) of zinc dust and 5.4 mL (0.054 mol) of ethyl acrylate in 20 mL of pyridine was added 4.2 g (0.018 mol) of $NiCl_2{\cdot}6H_2O$. The mixture was heated to 50° C., whereupon an exotherm ensued, and stirring was continued at 65° C. for 30 min. The resulting reddish-brown mixture was cooled to 25° C. and treated during 0.5 h with a solution of 10 g (0.018 mol) of 3β-tert-Butyldimethyl silyloxy-22-iodo-23,24-bisnorchola-5,7-diene (9), obtained in example 8b, in 30 mL of pyridine at a rate so as to maintain the temperature below 25° C. The mixture was stirred at 25° C. for 4 h, poured into 150 mL of EtOAc, and filtered through a pad of Celite. The pad was washed with EtOAc (2×100 mL), and the filtrate and washings were washed with 1.0 N HCl (4×150 mL), 200 mL of a solution of EDTA (80.0 g EDTA+80 g $NaHCO_3$ in 1.0 L of $H_2O$), and brine (2×100 mL). Dried the mixture over $Na_2SO_4$ and evaporated to give brownish solid of Ethyl-3β-tert-Butyldimethylsilyloxy-chola-5,7-diene-24-carboxylate (10) which was used directly in the next step.

An analytical sample was prepared by an additional purification by silicagel column chromatography using EtOAc:n-heptane (2:98) as an eluent. Concentration of collected pure fractions yielded desired product as thick white solid.

Appearance: White solid M.Pt: 98-100° C. GC purity: ~95% (RT: 28.87)

$^1$HNMR: δ 0.02-0.01 (6H, s) 0.78 (9H, s), 0.98 (3H, d), 1.14 (3H, t), 2.23 (2H, t), 2.53 (1H, dd), 2.68 (1H, dd), 4.1 (2H, q), 4.18 (1H, dddd), 5.97-6.00 (2H, dd).

Mass spectrum (m/e): 529 (M+1)

Example 10: 3β-tert-Butyldimethylsilyloxy-25-hydroxychola-5,7-diene (11)

To a stirred, cooled ice bath solution of 5.0 g (0.009 mol) of Ethyl-3β-tert-Butyldimethylsilyloxy-chola-5,7-diene-24-carboxylate (10) of example 9 in 100 mL of dry THF under nitrogen atmosphere was added 5.2 mL (0.0226 mol) of methyl magnesium bromide (3.0 M in ether) during 30 min. The mixture was stirred at ice bath temperature for 15 min and at room temperature for 2-3 h, cooled to 0° C., and carefully quenched with saturated $NH_4Cl$. The mass was extracted with 200 mL of EtOAc, washed with brine (250 mL), dried over $Na_2SO_4$, and evaporated in vacuo to give 4.8 g of crude 3β-tert-Butyldimethylsilyloxy-25-hydroxy-chola-5,7-diene (11).

The crude mass was further stirred with methanol, filtered, dried to get 4.1 g (87%) of desired product as a colorless solid. Recrystallization was carried out in methanol to give 3β-tert-Butyldimethylsilyloxy-25-hydroxychola-5,7-diene as white crystalline solid.

Analytical Data: Appearance: Colourless solid GC purity: >95%

$^1$HNMR: δ 0.02-0.01 (6H, s) 0.78 (9H, s), 1.00 (3H, d), 2.23 (1H, dd), 2.32 (1H, dd) 2.53 (1H, dd), 2.68 (1H, dd), 4.18 (1H, dddd), 5.97-6.01 (2H, dd).

Mass spectrum (m/e): 515 (M+1)

Example 11: 3β-25-Dihydroxycholesta-5,7-diene (provitamin of 25-Hydroxy vitamin D3) (IIB)

To 3β-tert-Butyldimethylsilyloxy-25-hydroxychola-5,7-diene (11), of example 10, 3β-tert-Butyldimethylsilyloxy-25-hydroxy-5,7-diene (4.0 g, 0.0076, mole) and $Bu_4NF\cdot 3H_2O$ (4.8 g, 0.015 mole) in THF (100 mL) were added and the mixture was stirred under argon at 40° C. for 4 h. This was followed by addition of EtOAc (200 mL) and the mixture washed with brine (100×3 mL). The organic phase was separated, dried over $Na_2SO_4$ and the solvent removed under reduced pressure. The residue was crystallized from MeOH.

Analytical Data: Yield: 2.7 g (90%) GC: 98% (RT: 10.05) M.Pt: 156-157° C.

$^1$H-NMR (400 MHz, $CDCl_3$): δ=0.60 (s, 3H), 0.94 (s, 3H), 0.96 (d, 3H), 1.19 (s, 6H), 3.66 (m, 1H), 5.39 (d, 1H), 5.55 (d, 1H).

The $^1$H NMR data correspond to those known from the literature.

$^{13}$C-NMR: (100 MHz, $CDCl_3$): δ 141.3, 139.8, 119.5, 116.3, 71.1, 70.4, 55.8, 54.4, 46.2, 44.4, 42.9, 40.8, 39.1, 38.3, 37.0, 36.3, 36.0, 32.0, 29.3, 29.2, 28.1, 23.0, 21.1, 20.8, 18.8, 16.3, 11.8.

Example 12: 25-OH Vitamin D3 (Calcifediol)

In a 1.5 litre tetrahydrofuran was dissolved 46.8 g of 25-OH7-dehydrocholesterol (IIB) of example 7, and the mixture was stirred in a magnetic stirrer under nitrogen atmosphere. To the mixture was added 1 g of butylated hydroxy toluene (BHT) and 1 g of sensitizer 5-(3-pyridyl)-2,2'-bithiophene and stirred for a while to obtain clear solution. Falling film apparatus was used to irradiate the solution continuously for 180 minutes at room temperature and the irradiation was carried out using ultraviolet rays from the medium pressure mercury lamp of wavelength 250-310 nm. The content of the pre vitamin D derivative of intended product was determined and monitored by high performance liquid chromatography (HPLC). After 180 minute irradiation reaction mixture was cooled to 0-5° C. for 30 minutes The solids separated out was filtered as first crop containing 25_OH 7-Dehydrocholesterol (50-60%).

The filtrate was concentrated to 20% of the original volume, cooled to 0-5° C. for 24 hrs and the separated solids were filtered as second crop that contained 25-OH 7-Dehydrocholesterol (15-20%).

The first and second crops were combined and reused in subsequent batches.

The filtrate was then evaporated under vacuum at 40-45° C. to get the crude compound which was then dissolved in 200 mL toluene and refluxed for 1-2 hr. The solvent was concentrated completely under vacuum to get crude reddish orange sticky mass (resin).

Yield: 20 g

The residue was purified by column chromatography over silica gel with Toluene:methyl ketone 1:99, 2:98, 4:96 & 5:95 to isolate pure 25-OH Vitamin D3/Calcifediol crystals which were recrystallized in acetone/water twice, filtered and dried to get highly pure crystals of Calcifediol.

Yield: 7.0 g

The Filtrate was further concentrated and kept for 2nd crystallization and the process of crystallization using acetone/water was carried out severally to isolate pure Calcifediol.

Analytical Data: Appearance: White crystalline solid HPLC: 99.9% (RT: 13.49)

$^1$H NMR (400 MHz, $CDCl_3$): δ 6.23 (d, 1H), 6.03 (d, 1H), 5.05 (br, 1H), 4.82 (br, 1H), 3.95 (m, 1H), 1.21 (s, 6H), 0.93 (d, 3H), 0.54 (s, 3H).

$^{13}$C-NMR (100 MHz, $CDCl_3$): δ 145.1, 142.2, 135.0, 122.4, 117.4, 112.4, 71.1, 69.1, 56.5, 56.3, 45.9, 45.8, 44.3, 40.5, 36.3, 36.1, 35.1, 31.9, 29.3, 29.1 28.9, 27.6, 23.5, 22.2, 20.8, 18.7, 11.9.

TABLE 1

| Sr no | Compound | % by HPLC | Potency |
|---|---|---|---|
| 1 | 25-OHVitamin D3/Calcifediol | 98-99.5% | 40 MIU |
| 3 | 25-OH7-Dehydrocholesterol | ND | NA |
| 4 | 25-OHTachysterol | 0.01% | NA |
| 5 | 25-OH Lumisterol | 0.01% | NA |
| 6 | 25-OH Trans Vitamin D3 | 0.05% | NA |

It will be understood that the above description is intended to be illustrative and not restrictive. The embodiments will be apparent to those in the art upon reviewing the above description. The scope of the invention should therefore, be determined not with reference to the above description but should instead be determined by the appended claims along with full scope of equivalents to which such claims are entitled.

We claim:

1. A process for the conversion of ergosterol to vitamin D3 of formula (I), wherein R=H, or calcifediol of formula (I), wherein R=OH:

(I)

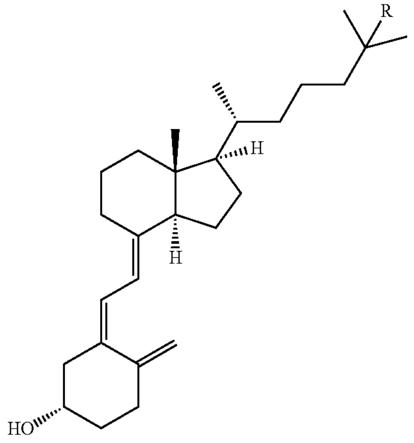

R = H (Vitamin D3)
R = OH (25-OH-Vitamin D3 [Calcifedio])

via a provitamin precursor of formula (II), wherein R=H or OH:

(II)

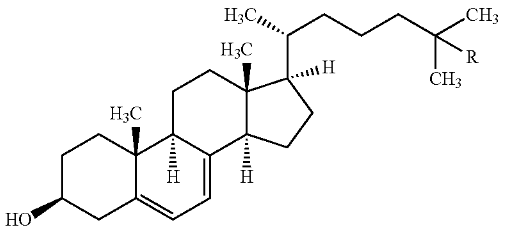

R = H (Provitamin D3)
R = OH (25-OH-Provitamin D3)

wherein the process comprises:

i. silylating ergosterol to obtain 3β-tert-butyldimethylsilyloxy-ergosta-5,7,22-triene;

ii. reacting 3β-tert-butyldimethylsilyloxy-ergosta-5,7,22-triene with 1,4-dihydrophthalazine-1,4-dione to obtain the Diels Alder adduct 3β-tert-Butyldimethylsilyloxy-5α,8α-(1,4-dioxo-1,2,3,4-tetrahydro-phthalazine-2,3-diyl)-23,24-bisnorchol-6-en-22-al;

iii. converting 3β-tert-Butyldimethylsilyloxy-5α,8α-(1,4-dioxo-1,2,3,4-tetrahydro-phthalazine-2,3-diyl)-23,24-bisnorchol-6-en-22-al to 3β-tert-Butyldimethylsilyloxy-22-hydroxy-23,24-bisnorchola-5,7-diene in one step with $LiAlH_4$;

iv. tosylating 3β-tert-Butyldimethylsilyloxy-22-hydroxy-23,24-bisnorchola-5,7-diene to obtain 3β-tert-Butyldimethylsilyloxy-22-tosyloxy-23,24-bisnorchola-5,7-diene;

v. converting 3β-tert-Butyldimethylsilyloxy-22-tosyloxy-23,24-bisnorchola-5,7-diene to the provitamin precursor of formula (II); and vi. irradiating the provitamin precursor of formula (II) in the presence of a photosensitizer, wherein the photosensitizer is 5-(3-pyridyl)-2,2'-bithiophene, to obtain the compound of formula (I); and vii. crystallizing the compound of formula (I).

2. The process of claim 1, wherein the step of converting 3β-tert-Butyldimethylsilyloxy-5α,8α-(1,4-dioxo-1,2,3,4-tetrahydro-phthalazine-2,3-diyl)-23,24-bisnorchol-6-en-22-al to 3β-tert-Butyldimethylsilyloxy-22-hydroxy-23,24-bisnorchola-5,7-diene in one step with $LiAlH_4$ is carried out in THF at a temperature of 45° C. for 3 hours.

3. The process of claim 1, wherein converting 3β-tert-Butyldimethylsilyloxy-22-tosyloxy-23,24-bisnorchola-5,7-diene to the provitamin precursor of formula (II) comprises reacting 3β-tert-Butyldimethylsilyloxy-22-tosyloxy-23,24-bisnorchola-5,7-diene with a Grignard reagent prepared from 1-Bromo-3-methylbutane in the presence of $CuBr{\cdot}Me_2S$, followed by desilylation with TBAF in THF to obtain 7-dehydrocholesterol of Formula (II), wherein R=H.

4. The process of claim 1, wherein converting 3β-tert-Butyldimethylsilyloxy-22-tosyloxy-23,24-bisnorchola-5,7-diene to the provitamin precursor of formula (II) comprises reacting 3β-tert-Butyldimethylsilyloxy-22-tosyloxy-23,24-bisnorchola-5,7-diene with a Grignard reagent prepared from 4-bromo-2-methyl-2-[(trimethyl silyl)oxy]butane in the presence of $CuBr{\cdot}Me_2S$, followed by desilylation with TBAF in THF to obtain 25-OH-Provitamin D3 of Formula (II), wherein R=OH.

5. The process of claim 3, wherein irradiating the provitamin precursor comprises irradiating 7-dehydrocholesterol of Formula (II), wherein R=H in the presence of the photosensitizer 5-(3-pyridyl)-2,2'-bithiophene using a medium pressure mercury lamp as a light source to obtain vitamin D3.

6. The process of claim 4, wherein irradiating the provitamin precursor comprises irradiating 25-OH-Provitamin D3 of formula (II), wherein R=OH, in the presence of the photosensitizer 5-(3-pyridyl)-2,2'-bithiophene using a medium pressure mercury lamp as a light source to obtain calcifediol.

7. The process of claim 1, wherein 3β-tert-Butyldimethylsilyloxy-5α,8α-(1,4-dioxo-1,2,3,4-tetrahydro-phthalazine-2,3-diyl)-23,24-bisnorchol-6-en-22-al is obtained by:

silylating a 3β-hydroxyl group of ergosterol to obtain 3β-tert-Butyldimethylsilyloxy-ergosta-5,7,22-triene;

converting 3β-tert-Butyldimethylsilyloxy-ergosta-5,7,22-triene to 3β-tert-butyldimethylsilyloxy-ergosta-5,7,22-triene-5α,8α-(1,4-dioxo-1,2,3,4-tetrahydrophthalazine-2,3-diyl) ergosta-6,22-diene by performing a hetero Diels-Alder reaction between 3β-tert-Butyldimethylsilyloxy-ergosta-5,7,22-triene and 1,4-dihydrophthalazine-1,4-dione;

carrying out ozonolysis of 3β-tert-butyldimethylsilyloxy-ergosta-5,7,22-triene-5α,8α-(1,4-dioxo-1,2,3,4-tetrahydrophthalazine-2,3-diyl) ergosta-6,22-diene to obtain 3β-tert-Butyldimethylsilyloxy-5α,8α-(1,4-dioxo-1,2,3,4-tetrahydro-phthalazine-2,3-diyl)-23,24-bisnorchol-6-en-22-al(4).

8. The process of claim 1, wherein converting 3β-tert-Butyldimethylsilyloxy-22-tosyloxy-23,24-bisnorchola-5,7-diene to the provitamin precursor of formula (II), wherein R=OH, comprises:

reacting 3β-tert-Butyldimethylsilyloxy-22-hydroxy-23,24-bisnorchola-5,7-diene with $PPh_3/I_2$ in imidazole to obtain the iodo compound 3β-tert-Butyldimethylsilyloxy-22-iodo-23,24-bisnorchola-5,7-diene; and converting the iodo compound to the provitamin precursor of formula (II), wherein R=OH.

9. The process of claim 1, wherein converting 3β-tert-Butyldimethylsilyloxy-22-tosyloxy-23,24-bisnorchola-5,7-diene to the provitamin precursor of formula (II), wherein R=OH, comprises reacting intermediate 3β-tert-Butyldimethylsilyloxy-22-tosyloxy-23,24-bisnorchola-5,7-diene with NaI/acetone at reflux to obtain the iodo compound 3β-tert-Butyldimethylsilyloxy-22-iodo-23,24-bisnorchola-5,7-diene; and converting the iodo compound to the provitamin precursor of formula (II), wherein R=OH.

10. A process for the conversion of ergosterol to calcifediol of formula (I), wherein R=OH, via a provitamin precursor of formula (II), wherein R=OH:

(I)

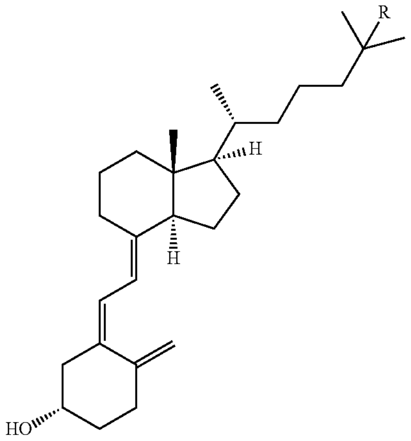

R = OH , (II)

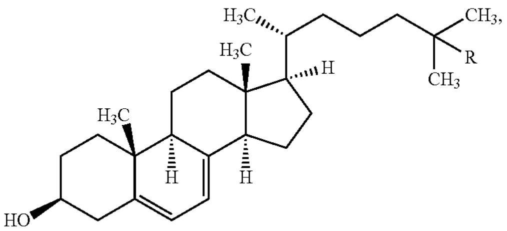

R = OH wherein the process comprises:

iii. silylating ergosterol to obtain 3β-tert-butyldimethylsilyloxy-ergosta-5,7,22-triene;

iv. reacting 3β-tert-butyldimethylsilyloxy-ergosta-5,7,22-triene with 1,4-dihydrophthalazine-1,4-dione to obtain the Diels Alder adduct 3β-tert-Butyldimethylsilyloxy-5α,8α-(1,4-dioxo-1,2,3,4-tetrahydro-phthalazine-2,3-diyl)-23,24-bisnorchol-6-en-22-al;

iii. converting 3β-tert-Butyldimethylsilyloxy-5α,8α-(1,4-dioxo-1,2,3,4-tetrahydro-phthalazine-2,3-diyl)-23,24-bisnorchol-6-en-22-al to 3β-tert-Butyldimethylsilyloxy-22-hydroxy-23,24-bisnorchola-5,7-diene in one step with $LiAlH_4$;

iv. tosylating 3β-tert-Butyldimethylsilyloxy-22-hydroxy-23,24-bisnorchola-5,7-diene to obtain 3β-tert-Butyldimethylsilyloxy-22-tosyloxy-23,24-bisnorchola-5,7-diene;

V. converting 3β-tert-Butyldimethylsilyloxy-22-hydroxy-23,24-bisnorchola-5,7-diene into an iodo compound; and converting the iodo compound to the provitamin precursor of formula (II), wherein R=OH; and vi. irradiating the provitamin precursor of formula (II) in the presence of a photosensitizer, wherein the photosensitizer is 5-(3-pyridyl)-2,2'-bithiophene, to obtain the compound of formula (I);

wherein converting the iodo compound to the provitamin precursor of formula (II), wherein R=OH, comprises:

alkylating the iodo compound with a reaction product of $NiCl_2$ and ethyl acrylate to yield ethyl-3β-tert-butyldimethylsilyloxy-chola-5,7-diene-24-carboxylate, wherein the reaction product is prepared in situ;

reacting ethyl-3β-tert-butyldimethylsilyloxy-chola-5,7-diene-24-carboxylate with methyl magnesium bromide to obtain 3β-tert-Butyldimethylsilyloxy-25-hydroxychola-5,7-diene, followed by desilylation with TBAF in THF to yield 25-OH-provitamin D3 of formula (II), wherein R=OH.

11. The process of claim 9, wherein converting the iodo compound to the provitamin precursor of formula (II) of formula (II), wherein R=OH, comprises:

alkylating the iodo compound with a reaction product of $NiCl_2$ and ethyl acrylate to yield ethyl-3β-tert-butyldimethylsilyloxy-chola-5,7-diene-24-carboxylate, wherein the reaction product is prepared in situ;

reacting ethyl-3β-tert-butyldimethylsilyloxy-chola-5,7-diene-24-carboxylate with methyl magnesium bromide to obtain 3β-tert-Butyldimethylsilyloxy-25-hydroxychola-5,7-diene, followed by desilylation with TBAF in THF to yield 25-OH-provitamin D3 of formula (II), wherein R=OH.

12. The process of claim 1, wherein each step of the process is carried out in a solvent selected from the group consisting of polar solvents, non-polar solvents; protic solvents, and aprotic solvents.

13. The process of claim 1, wherein each step of the process is carried out in a solvent selected from the group consisting of C1-C6 alcohols, ethers, ketones, DMF, DMSO, halogenated hydrocarbons, C1-C7 straight- or branched-chain hydrocarbons, aromatic hydrocarbons, pyridine, esters, acetonitrile, and mixtures thereof.

14. The process of claim 1, wherein each step of the process is carried out at a temperature of between −80° C. to 120° C.

* * * * *